US012011371B2

(12) United States Patent
Wolfson et al.

(10) Patent No.: US 12,011,371 B2
(45) Date of Patent: Jun. 18, 2024

(54) SYSTEM AND METHOD FOR SURGICALLY-PREPARING A PATIENT'S FEMUR

(71) Applicant: DePuy Ireland Unlimited Company, Ringaskiddy (IE)

(72) Inventors: David R. Wolfson, Leeds (GB); James E. Barnett, Leeds (GB); Charles L. Penninger, Warsaw, IN (US); Michael R. Reeve, North Yorkshire (GB); Philip R. Meggett, Lincoln (GB); Rebecca L. Chaney, Warsaw, IN (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 0 days.

(21) Appl. No.: 17/884,066

(22) Filed: Aug. 9, 2022

(65) Prior Publication Data

US 2022/0378585 A1    Dec. 1, 2022

Related U.S. Application Data

(63) Continuation of application No. 16/748,010, filed on Jan. 21, 2020, now Pat. No. 11,406,512, which is a
(Continued)

(51) Int. Cl.
*A61F 2/46*       (2006.01)
*A61B 17/15*      (2006.01)
(Continued)

(52) U.S. Cl.
CPC ............ *A61F 2/461* (2013.01); *A61B 17/155* (2013.01); *A61B 17/157* (2013.01);
(Continued)

(58) Field of Classification Search
CPC .. A61F 2/461; A61F 2/46; A61F 2/385; A61F 2/3859; A61F 2/389; A61F 2/4684;
(Continued)

(56) References Cited

U.S. PATENT DOCUMENTS 3,727,928 A    4/1973  Benjamin
4,710,075 A   12/1987  Davison
(Continued)

FOREIGN PATENT DOCUMENTS

CH         706593 A1   12/2013
CN       102892367 A    1/2013
(Continued)

OTHER PUBLICATIONS

Attune Knee System Surg. Tech., 2013, 73 Pgs.
(Continued)

*Primary Examiner* — Jessica Weiss
(74) *Attorney, Agent, or Firm* — Barnes & Thornburg LLP

(57) ABSTRACT

An orthopaedic joint replacement system is shown and described. The system includes a number of prosthetic components configured to be implanted into a patient's knee. The system also includes a number of surgical instruments configured for use in preparing the bones of the patient's knee to receive the implants. A method or technique for using the surgical instruments to prepare the bones is also disclosed.

19 Claims, 22 Drawing Sheets

Related U.S. Application Data continuation of application No. 15/598,620, filed on May 18, 2017, now Pat. No. 10,537,440.

(60) Provisional application No. 62/338,468, filed on May 18, 2016.

(51) Int. Cl.
| | | |
|---|---|---|
| *A61B 17/16* | (2006.01) | |
| *A61B 17/17* | (2006.01) | |
| *A61F 2/38* | (2006.01) | |
| *A61B 17/14* | (2006.01) | |
| *A61B 17/72* | (2006.01) | |
| *A61B 17/88* | (2006.01) | |
| *A61B 90/00* | (2016.01) | |
| *A61F 2/30* | (2006.01) | |

(52) U.S. Cl.
CPC ...... *A61B 17/1675* (2013.01); *A61B 17/1764* (2013.01); *A61F 2/385* (2013.01); *A61F 2/3859* (2013.01); *A61F 2/389* (2013.01); *A61F 2/4684* (2013.01); *A61B 17/14* (2013.01); *A61B 17/72* (2013.01); *A61B 17/8872* (2013.01); *A61B 17/8875* (2013.01); *A61B 2090/034* (2016.02); *A61B 2090/036* (2016.02); *A61F 2002/30736* (2013.01); *A61F 2002/30738* (2013.01); *A61F 2002/3863* (2013.01); *A61F 2002/4668* (2013.01); *A61F 2002/4687* (2013.01)

(58) Field of Classification Search
CPC .... A61F 2002/30736; A61F 2002/3863; A61F 2002/4668; A61F 2002/4687; A61B 17/155; A61B 17/1675; A61B 17/1764; A61B 2090/034; A61B 2090/036; A61B 17/14; A61B 17/72; A61B 17/8872; A61B 17/8875
USPC .......................................... 623/20.14–20.36
See application file for complete search history.

(56) References Cited

U.S. PATENT DOCUMENTS

| | | | |
|---|---|---|---|
| 4,952,213 | A | 8/1990 | Bowman et al. |
| 5,053,037 | A | 10/1991 | Lackey |
| 5,100,409 | A | 3/1992 | Coates et al. |
| 5,176,684 | A | 1/1993 | Ferrante et al. |
| 5,356,414 | A | 10/1994 | Cohen et al. |
| 5,415,662 | A | 5/1995 | Ferrante et al. |
| 5,569,259 | A | 10/1996 | Ferrante et al. |
| 5,571,194 | A | 11/1996 | Gabriel |
| 5,601,563 | A | 2/1997 | Burke et al. |
| 5,613,970 | A | 3/1997 | Houston et al. |
| 5,634,927 | A | 6/1997 | Houston et al. |
| 5,681,316 | A | 10/1997 | DeOrio et al. |
| 5,683,397 | A | 11/1997 | Vendrely et al. |
| 5,702,460 | A | 12/1997 | Carls et al. |
| 5,720,752 | A | 2/1998 | Elliott et al. |
| 5,735,856 | A | 4/1998 | McCue et al. |
| 5,769,854 | A | 6/1998 | Bastian et al. |
| 5,931,841 | A | 8/1999 | Ralph |
| 5,976,147 | A | 11/1999 | LaSalle et al. |
| 6,033,410 | A | 3/2000 | McLean et al. |
| 6,488,687 | B1 | 12/2002 | Masini |
| 6,575,980 | B1 | 6/2003 | Robie et al. |
| 6,945,145 | B1 | 9/2005 | Kesinger |
| 7,457,327 | B2 | 11/2008 | Nakano et al. |
| 7,497,874 | B1 | 3/2009 | Metzger et al. |
| 7,744,600 | B2 | 6/2010 | Rangaiah et al. |
| 7,963,968 | B2 | 6/2011 | Dees, Jr. |
| 8,002,777 | B2 | 8/2011 | Fox et al. |
| 8,038,681 | B2 | 10/2011 | Koenemann |
| 8,187,280 | B2 | 5/2012 | May et al. |
| 8,277,450 | B2 * | 10/2012 | Dees, Jr. .............. A61B 17/154 |
| | | | 279/42 |
| 8,377,141 | B2 | 2/2013 | McMinn |
| 8,425,524 | B2 | 4/2013 | Aker et al. |
| 8,771,280 | B2 | 7/2014 | Bailey et al. |
| 8,834,473 | B2 | 9/2014 | Dees, Jr. et al. |
| 8,979,847 | B2 | 3/2015 | Belcher et al. |
| 8,986,310 | B2 | 3/2015 | Bailey et al. |
| 9,028,501 | B2 | 5/2015 | Thomas et al. |
| 9,113,915 | B2 | 8/2015 | Thomas et al. |
| 9,232,950 | B2 * | 1/2016 | Chaney .............. A61B 17/1764 |
| 9,579,113 | B2 | 2/2017 | Thomas et al. |
| 9,636,122 | B2 | 5/2017 | Chaney et al. |
| 9,962,173 | B2 | 5/2018 | Thomas et al. |
| 10,363,148 | B2 * | 7/2019 | Lashure .............. A61B 17/1631 |
| 10,537,148 | B2 | 1/2020 | Hanson et al. |
| 11,096,735 | B2 | 8/2021 | Rohlfing et al. |
| 2001/0001121 | A1 * | 5/2001 | Lombardo .......... A61B 17/1668 |
| | | | 606/89 |
| 2003/0114859 | A1 | 6/2003 | Grusin et al. |
| 2004/0039450 | A1 | 2/2004 | Griner et al. |
| 2004/0078043 | A1 | 4/2004 | Masini |
| 2004/0087960 | A1 | 5/2004 | Kinnett |
| 2004/0153087 | A1 | 8/2004 | Sanford et al. |
| 2004/0225368 | A1 | 11/2004 | Plumet et al. |
| 2004/0264082 | A1 | 12/2004 | Suliman et al. |
| 2004/0265082 | A1 | 12/2004 | Abrams |
| 2005/0192588 | A1 | 9/2005 | Garcia |
| 2006/0008771 | A1 | 1/2006 | Courvoisier |
| 2006/0173463 | A1 | 8/2006 | Dees, Jr. |
| 2006/0195113 | A1 | 8/2006 | Masini |
| 2006/0200163 | A1 | 9/2006 | Roger et al. |
| 2006/0241634 | A1 | 10/2006 | Tuttle et al. |
| 2007/0010890 | A1 | 1/2007 | Collazo |
| 2007/0073305 | A1 | 3/2007 | Lionberger, Jr. et al. |
| 2007/0173850 | A1 | 7/2007 | Rangaiah et al. |
| 2008/0091273 | A1 | 4/2008 | Hazebrouck |
| 2008/0161824 | A1 | 7/2008 | McMillen |
| 2008/0177337 | A1 | 7/2008 | McGovern et al. |
| 2008/0183177 | A1 | 7/2008 | Fox et al. |
| 2008/0228189 | A1 * | 9/2008 | Fox ..................... A61B 17/155 |
| | | | 606/88 |
| 2008/0312659 | A1 | 12/2008 | Metzger et al. |
| 2009/0088762 | A1 | 4/2009 | Koenemann |
| 2009/0088763 | A1 | 4/2009 | Aram et al. |
| 2009/0125114 | A1 * | 5/2009 | May ..................... A61F 2/38 |
| | | | 623/20.14 |
| 2009/0204115 | A1 | 8/2009 | Dees, Jr. et al. |
| 2009/0222008 | A1 | 9/2009 | Hogg et al. |
| 2010/0076441 | A1 | 3/2010 | May et al. |
| 2010/0094301 | A1 | 4/2010 | Dees et al. |
| 2010/0121334 | A1 | 5/2010 | Couture et al. |
| 2010/0234850 | A1 | 9/2010 | Dees, Jr. et al. |
| 2011/0093081 | A1 | 4/2011 | Chana et al. |
| 2011/0213378 | A1 | 9/2011 | Dees, Jr. |
| 2011/0218541 | A1 | 9/2011 | Bailey et al. |
| 2011/0307067 | A1 | 12/2011 | Dees |
| 2012/0136359 | A1 | 5/2012 | Grunder et al. |
| 2012/0310246 | A1 * | 12/2012 | Belcher ............... A61B 17/157 |
| | | | 606/89 |
| 2012/0323334 | A1 | 12/2012 | Jones et al. |
| 2013/0012941 | A1 | 1/2013 | Dees, Jr. et al. |
| 2013/0144293 | A1 | 6/2013 | Wilkinson |
| 2013/0144296 | A1 | 6/2013 | Yoko et al. |
| 2013/0165936 | A1 | 6/2013 | Myers |
| 2013/0197654 | A1 * | 8/2013 | Samuelson ............ A61F 2/3886 |
| | | | 623/20.35 |
| 2013/0325014 | A1 * | 12/2013 | Sordelet ............ A61B 17/1764 |
| | | | 606/82 |
| 2013/0325016 | A1 | 12/2013 | Sordelet et al. |
| 2013/0325018 | A1 * | 12/2013 | Thomas ............... A61B 17/164 |
| | | | 606/88 |
| 2013/0325019 | A1 | 12/2013 | Thomas et al. |
| 2013/0325021 | A1 * | 12/2013 | Sordelet ............... A61B 17/155 |
| | | | 606/89 |
| 2013/0325136 | A1 * | 12/2013 | Thomas ............... A61B 17/1735 |
| | | | 623/20.32 |

(56) References Cited

U.S. PATENT DOCUMENTS

| | | | |
|---|---|---|---|
| 2014/0114318 A1* | 4/2014 | May | A61F 2/30721 606/88 |
| 2014/0148811 A1 | 5/2014 | Reeve et al. | |
| 2014/0243835 A1 | 8/2014 | Teeny et al. | |
| 2014/0276836 A1* | 9/2014 | Chaney | A61B 17/155 606/88 |
| 2014/0276837 A1* | 9/2014 | Chaney | A61B 17/155 606/88 |
| 2014/0276857 A1* | 9/2014 | Major | A61F 2/3868 606/88 |
| 2014/0276858 A1* | 9/2014 | Major | A61B 17/157 606/88 |
| 2016/0089159 A1 | 3/2016 | Ardito et al. | |
| 2016/0089161 A1 | 3/2016 | Ardito et al. | |
| 2017/0333211 A1 | 11/2017 | Flakne | |
| 2017/0333212 A1 | 11/2017 | Wolfson et al. | |
| 2017/0333213 A1 | 11/2017 | Wolfson et al. | |
| 2017/0333215 A1 | 11/2017 | Wolfson et al. | |

FOREIGN PATENT DOCUMENTS

| | | |
|---|---|---|
| CN | 101742972 B | 1/2015 |
| CN | 101849864 B | 6/2015 |
| CN | 101879099 B | 8/2015 |
| CN | 104042256 B | 12/2017 |
| CN | 104042310 B | 6/2018 |
| EP | 0947169 A2 | 10/1999 |
| EP | 0993807 B1 | 4/2005 |
| EP | 1609560 B1 | 5/2009 |
| EP | 2145590 B1 | 5/2012 |
| EP | 2777556 B1 | 9/2017 |
| EP | 2777550 B1 | 5/2020 |
| FR | 2748389 A1 | 11/1997 |
| FR | 2752519 B3 | 10/1998 |
| FR | 2943528 B1 | 6/2011 |
| GB | 2323037 B | 6/2001 |
| JP | H11104155 A | 4/1999 |
| JP | 2009006066 A | 1/2009 |
| JP | 2010057527 A | 3/2010 |
| JP | 2013521991 A | 6/2013 |
| JP | 2014502185 A | 1/2014 |
| JP | 2014180563 A | 9/2014 |
| JP | 2016067939 A | 5/2016 |
| RU | 2148960 C1 | 5/2000 |
| RU | 2168315 C2 | 6/2001 |
| RU | 2332181 C2 | 8/2008 |
| WO | 1996025123 A2 | 8/1996 |
| WO | 1997030661 A1 | 8/1997 |
| WO | 1998052499 A1 | 11/1998 |
| WO | 2000013597 A1 | 3/2000 |
| WO | 2007041644 A1 | 4/2007 |
| WO | 2007114841 A1 | 10/2007 |
| WO | 2010019284 A1 | 2/2010 |
| WO | 2012066306 A1 | 5/2012 |

OTHER PUBLICATIONS

Australian Examination Report, App. No. 2017268380, dated Jun. 21, 2021, 4 Pages.
Biomet, Vanguard SSK, Revision System, Surg. Tech. Feb. 2008, 64 Pgs.
Chinese Search Report, App. No. 201780030765.1, dated Jan. 2010, 3 Pages.
Chinese Search Report, App. No. 201780030942.6, dated Mar. 22, 2021, 2 Pages.
Chinese Search Report, Chinese App. No. 201780030942.6, dated Aug. 27, 2020, 6 Pages.
Declaration of Gary M. Lindsay Dated Dec. 23, 14, 5 Pgs.
Depuy Orthopaedics, Inc., Sigma Revision & MBT Revision Tray, Surg. Tech, 2008, 82 Pgs.
English Translation of Chinese Search Report, App. No. 201780030942.6 dated Mar. 22, 2021, 2 Pages.
GMK Revision, Surg. Tech. Ref. 99.27.12 US Rev. 1, 1999, 74 Pgs.
Indian Examination Report, App. No. 201817041134, dated Jun. 1, 2021, 4 Pages.
Int'l SR, PCT/US2017/033278, dated Nov. 21, 17, 6 Pgs.
Int'l SR, PCT/US2017/033278, dated Aug. 30, 17, 13 Pgs.
Int'l SR, PCT/US2017/033295, dated Dec. 18, 17, 8 Pgs.
Int'l SR, PCT/US2017/033295, dated Sep. 4, 17, 14 Pgs.
Int'l SR, PCT/US2017/033307, dated Sep. 25, 17, 13 Pgs.
Japanese Search Report, App. No. 2018-560493, dated Mar. 3, 2021, 5 Pages.
Japanese Search Report, App. No. 2018-560584, dated Mar. 16, 2021, 5 Pages.
LCS High Performance Instruments, Surg. Tech, 2008, 44 Pgs.
PFC SIGMA Rotating Platform Knee System With MBT Tray, Primary Procedure With a Curved or Posterior Stabilised Implant, 2003, 43 Pgs.
PFC Sigma RP-F, Specialist 2 Instruments, Surg. Tech, Performance in Flexion, 2007, 32 Pgs.
Redacted Memorandum With Appendix A, Dated Jan. 26, 2010, Outlining a Surgical Instrument Evaluation That Commenced in 2010, 37 Pgs.
Reinstall Wave 1 Evaluation Surg. Tech, Used During the Surgical Instrument Evaluation That Commenced in 2010, 36 Pgs.
Russian Search Report, Int. App. No. PCT/US2017/033278, dated Nov. 24, 2020, 2 Pages.
Sigma High Performance Instruments, Classic Surg. Tech., 2010, 52 Pgs.
Sigma High Performance Instruments, Design Rationale, 2007, 12 Pgs.
Smith & Nephew, Legion, Revision Knee System, Surg. Tech., 2005, 40 Pgs.
Synvasive Technology, Inc., eLIBRA Dynamic Knee Balancing System, Magnetic Augments, Cited on May 17, 2016, in U.S. Appl. No. 15/080,415.
Tray Configuration Cards Showing the Instruments Used During the Surgical Instrument Evaluation That Commenced in 2010, 8 Pgs.
Zimmer Nexgen Lcck, Surg. Tech. for Use With Lcck 4-in-1 Instrument, 2009, 52 Pgs.

* cited by examiner

SYSTEM AND METHOD FOR SURGICALLY-PREPARING A PATIENT'S FEMUR

The present application claims priority to U.S. patent application Ser. No. 16/748,010, now U.S. Pat. No. 11,406,512, which claim priority to U.S. patent application Ser. No. 15/598,620, now U.S. Pat. No. 10,537,440, which claims priority to U.S. Patent Application Ser. No. 62/338,468, filed May 18, 2016, each of which is herein incorporated by reference in its entirety.

CROSS-REFERENCE TO RELATED APPLICATIONS

Cross reference is made to U.S. Patent Application Ser. No. 62/338,276 entitled "SYSTEM AND METHOD FOR PREPARING A PATIENT'S FEMUR IN AN ORTHOPAEDIC JOINT REPLACEMENT PROCEDURE;" and U.S. Patent Application Ser. No. 62/338,284 entitled "SYSTEM AND METHOD FOR PREPARING A PATIENT'S TIBIA IN AN ORTHOPAEDIC JOINT REPLACEMENT PROCEDURE," each of which is assigned to the same assignee as the present application, each of which is filed concurrently herewith, and each of which is hereby incorporated by reference.

Cross reference is made to U.S. patent application Ser. No. 15/598,619, now U.S. Pat. No. 10,537,439 entitled "ORTHOPAEDIC INSTRUMENT SYSTEM FOR SURGICALLY-PREPARING A PATIENT'S FEMUR," which is assigned to the same assignee as the present application, which is filed concurrently herewith, and which is hereby incorporated by reference.

TECHNICAL FIELD

The present disclosure relates generally to an orthopaedic prosthesis system, including prosthetic components and instruments for use in the performance of an orthopaedic joint replacement procedure, and more particularly to orthopaedic prosthetic components and surgical instruments for use in the performance of a knee replacement procedure.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur From time-to-time, a revision knee surgery may need to be performed on a patient. In such a revision knee surgery, the previously-implanted knee prosthesis, sometimes referred to a "primary knee prosthesis," is surgically removed and a replacement or revision knee prosthesis is implanted. In some revision knee surgeries, all of the components of the primary knee prosthesis, including, for example, the tibial tray, the femoral component, and the polymer bearing, may be surgically removed and replaced with revision prosthetic components. In other revision knee surgeries, only part of the previously-implanted knee prosthesis may be removed and replaced.

During a revision knee surgery, the orthopaedic surgeon typically uses a variety of different orthopaedic surgical instruments such as, for example, cutting blocks, surgical reamers, drill guides, prosthetic trials, and other surgical instruments to prepare the patient's bones to receive the knee prosthesis. Other orthopaedic surgical instruments such as trial components may be used to size and select the components of the knee prosthesis that will replace the patient's natural joint. Trial components may include a femoral trial that may be used to size and select a prosthetic femoral component, a tibial tray trial that may be used to size and select a prosthetic tibial tray, and a stem trial that may be used to size and select a prosthetic stem component.

SUMMARY

An orthopaedic joint replacement system is shown and described. The system includes a number of prosthetic components configured to be implanted into a patient's knee. The system also includes a number of surgical instruments configured for use in preparing the bones of the patient's knee to receive the implants. A method or technique for using the surgical instruments to prepare the bones is also disclosed.

According to one aspect of the disclosure, an orthopaedic surgical instrument system includes a femoral cutting block including a plurality of cutting guide slots and an offset guide. The offset guide includes a mounting bracket configured to be coupled to the femoral cutting block. The mounting bracket has a distal surface and an opening defined in the distal surface. The offset guide also includes an adaptor body positioned in the opening defined in the mounting bracket. The adaptor body extends along a first longitudinal axis and includes a head plate that is pivotally coupled to the mounting bracket. The offset guide also includes an elongated shaft pivotally coupled to the adaptor body. The elongated shaft extends along a second longitudinal axis spaced apart from the first longitudinal axis. An intramedullary orthopaedic surgical instrument is configured to be coupled to the elongated shaft and sized to be inserted into a medullary canal of a patient's femur.

In some embodiments, the elongated shaft may have a triangular-shaped connector. The intramedullary orthopaedic surgical instrument may have an opening sized to receive the triangular-shaped connector of the elongated shaft. In some embodiments, the intramedullary orthopaedic surgical instrument may have a stem stabilizer configured to be coupled to the elongated shaft. A stem trial may be configured to be coupled to the stem stabilizer.

In some embodiments, the distal surface of the mounting bracket may define a first plane. The first longitudinal axis may extend at an oblique angle relative to the first plane. In some embodiments, the head plate may have a distal surface that defines a second plane that extends at an oblique angle relative to the first plane and may be orthogonal to the first longitudinal axis.

In some embodiments, a positioning block may have a main body, a first arm extending outwardly from the main body, and a second arm extending outwardly from the main body parallel to, and spaced apart from, the first arm. The cutting block may have a mounting slot sized to receive a tip of the first arm to couple the positioning block to the cutting block.

In some embodiments, an offset indicator may have a plug sized to be received in an aperture defined in the head plate of the adaptor body. The offset indicator may have a plurality of visual indicia to indicate an offset orientation of a prosthetic femoral component assembly. The offset indicator may be operable to pivot the head plate relative to the mounting bracket. In some embodiments, the mounting bracket may have a visual indicator configured to be aligned with at least one of the plurality of visual indicia of the offset indicator to indicate a planned offset orientation of a prosthetic femoral component. In some embodiments, the plug may have an alignment tab. The head plate may have an alignment slot sized to receive the alignment tab to position the offset indicator in a predetermined orientation relative to the offset guide.

In some embodiments, a surgical handle may have a locking flange pivotable between a locked position and an unlocked position. The head plate of the offset guide may have an annular rim sized to receive the locking flange to secure the surgical handle to the offset guide.

According to another aspect of the disclosure, an orthopaedic surgical instrument system includes a mounting bracket configured to be coupled to a femoral cutting block. The mounting bracket has a distal surface and an opening defined in the distal surface. An adaptor body is positioned in the opening defined in the mounting bracket. The adaptor body extends along a first longitudinal axis and includes a head plate that is pivotally coupled to the mounting bracket. An elongated shaft is pivotally coupled to the adaptor body. The elongated shaft extends along a second longitudinal axis spaced apart from the first longitudinal axis and includes a connector at its proximal end. A sleeve is positioned on the elongated shaft between the adaptor body and the connector. An intramedullary orthopaedic surgical instrument is coupled to the connector of the elongated shaft and sized to be inserted into a medullary canal of a patient's femur. The sleeve is movable along the elongated shaft between (i) a first position in which the sleeve engages the intramedullary orthopaedic surgical instrument to secure the intramedullary orthopaedic surgical instrument to the elongated shaft, and (ii) a second position in which the sleeve is spaced apart from the intramedullary orthopaedic surgical instrument.

In some embodiments, the connector may be triangular-shaped. The intramedullary orthopaedic surgical instrument may have an opening sized to receive the triangular-shaped connector. In some embodiments, the sleeve may have a threaded outer surface and the intramedullary orthopaedic surgical instrument may have a threaded inner surface that engages the threaded outer surface when the sleeve is in the first position. In some embodiments, the opening of the intramedullary orthopaedic surgical instrument may have a plurality of slots defined in the threaded inner surface of the intramedullary orthopaedic surgical instrument.

In some embodiments, the intramedullary orthopaedic surgical instrument may have a stem stabilizer coupled to the connector of the elongated shaft.

In some embodiments, an offset indicator may be configured to be coupled to the adaptor body. The offset indicator may have a plurality of visual indicia to indicate an offset orientation of a prosthetic femoral component assembly. The offset indicator may be operable to pivot the head plate and the adaptor body relative to the mounting bracket.

According to yet another aspect of the disclosure, an orthopaedic surgical instrument system includes an offset guide. The offset guide includes a mounting bracket configured to be coupled to a femoral cutting block. The mounting bracket has a distal surface and an opening defined in the distal surface. An adaptor body is positioned in the opening defined in the mounting bracket. The adaptor body extends along a first longitudinal axis and includes a head plate that is pivotally coupled to the mounting bracket. An elongated shaft is pivotally coupled to the adaptor body. The elongated shaft extends along a second longitudinal axis spaced apart from the first longitudinal axis and includes a connector sized to receive an intramedullary orthopaedic surgical instrument. An offset indicator is configured to be coupled to the head plate of the adaptor body. The offset indicator includes a plurality of visual indicia to indicate an offset orientation of a prosthetic femoral component assembly. When the elongated shaft is prevented from rotating about the second longitudinal axis, the offset indicator is operable to pivot the head plate relative to the mounting bracket about the first longitudinal axis and pivot the head plate relative to the elongated shaft about the second longitudinal axis.

In some embodiments, the offset guide also may have a sleeve positioned on the elongated shaft. The sleeve may be movable along the elongated shaft between a first position in which a threaded section of the sleeve engages the intramedullary orthopaedic surgical instrument to secure the intramedullary orthopaedic surgical instrument to the elongated shaft, and a second position in which the sleeve may be spaced apart from the intramedullary orthopaedic surgical instrument. In some embodiments, the connector may be triangular-shaped.

In some embodiments, the offset indicator may have an alignment tab. The head plate may have an alignment slot sized to receive the alignment tab to position the offset indicator in a predetermined orientation relative to the offset guide.

According to an aspect of the disclosure, a method of performing an orthopaedic surgical procedure includes aligning a distal end of an intramedullary orthopaedic surgical instrument with a proximal end of an offset guide. The method also includes positioning a connector at the proximal end of the offset guide in an opening defined in the distal end of the intramedullary orthopaedic surgical instrument to prevent relative rotational movement between the proximal end of the offset guide and the intramedullary orthopaedic surgical instrument. The method also includes advancing the intramedullary orthopaedic surgical instrument over the connector. The method also includes engaging a sleeve with the intramedullary orthopaedic surgical instrument to secure the intramedullary orthopaedic surgical instrument to the offset guide.

In some embodiments, engaging the sleeve with the intramedullary orthopaedic surgical instrument may require advancing the sleeve toward the proximal end of the offset guide and engaging a threaded outer surface of the sleeve with a threaded inner surface of the intramedullary orthopaedic surgical instrument. In some embodiments, positioning the connector at the proximal end of the offset guide in the opening defined in the distal end of the intramedullary orthopaedic surgical instrument may require positioning a triangular-shaped connector into a plurality of slots defined in the threaded inner surface of the intramedullary orthopaedic surgical instrument.

In some embodiments, the method may require securing a stem stabilizer to a stem trial to form the intramedullary orthopaedic surgical instrument.

In some embodiments, the method may require inserting the intramedullary orthopaedic surgical instrument into an opening defined in a distal end of a patient's femur. The method may require rotating a distal end of the offset guide about a longitudinal axis extending through the intramedullary orthopaedic surgical instrument to determine an offset orientation for a prosthetic femoral component. In some embodiments, the method may require securing the distal end of the offset guide to a femoral cutting block including a plurality of cutting slots. Rotating the distal end of the offset guide may require rotating the femoral cutting block relative to a distal surface of the patient's femur. In some embodiments, the method may require attaching an offset indicator to the distal end of the offset guide. Rotating the distal end of the offset guide may require rotating the offset indicator about a second longitudinal axis extending parallel to, and spaced apart from, the longitudinal axis extending through the intramedullary orthopaedic surgical instrument.

In some embodiments, the method may require attaching a first arm of a femoral positioning block to the cutting block. The method may require positioning a second arm of the femoral positioning block on a proximal end of the patient's tibia such that a predetermined gap may be defined between the patient's tibia and the femoral cutting block. Rotating the distal end of the offset guide may require adjusting a distance between the patient's tibia and the patient's femur while rotating the cutting block relative to a distal surface of the patient's femur. In some embodiments, the method may require resecting a portion of the distal end of the patient's femur. In some embodiments, the method may require detaching the offset guide from the femoral cutting block and removing the intramedullary orthopaedic surgical instrument from the opening in the patient's femur.

According to another aspect of the disclosure, a method of performing an orthopaedic surgical procedure includes securing an offset guide to a femoral cutting block. The method also includes inserting an elongated shaft of the offset guide into an opening defined in distal end of a patient's femur, wherein the elongated shaft extends along a first longitudinal axis. The method also includes attaching an offset indicator to the distal end of the offset guide. The method also includes rotating the offset indicator about a second longitudinal axis extending parallel to, and spaced apart from, the first longitudinal axis to rotate the femoral cutting block about the first longitudinal axis and determine an offset orientation for a prosthetic femoral component.

In some embodiments, the method may require securing an intramedullary orthopaedic surgical instrument to the offset guide such that the first longitudinal axis extends along the intramedullary orthopaedic surgical instrument. In some embodiments, rotating the offset indicator about the second longitudinal axis may require rotating a head plate of the offset guide with the offset indicator about the second longitudinal axis, such that the offset guide may be secured to the femoral cutting block such that the femoral cutting block may be prevented from rotating relative to the second longitudinal axis. In some embodiments, the method may require attaching a first arm of a femoral positioning block to the femoral cutting block. The method may require positioning a second arm of the femoral positioning block on a proximal end of the patient's tibia such that a predetermined gap may be defined between the patient's tibia and the femoral cutting block. Rotating the offset indicator about the second longitudinal axis may require adjusting a distance between the patient's tibia and the patient's femur while rotating the cutting block relative to a distal surface of the patient's femur. In some embodiments, the method may require resecting a portion of the distal end of the patient's femur.

According to another aspect of the disclosure, a method of performing an orthopaedic surgical procedure includes securing an intramedullary orthopaedic surgical instrument to an offset guide. The method also includes securing the offset guide to a femoral cutting block. The method also includes inserting the intramedullary orthopaedic surgical instrument into an opening defined in a distal end of a patient's femur. The method also includes attaching a first arm of a femoral positioning block to the femoral cutting block. The method also includes positioning a second arm of the femoral positioning block on a proximal end of the patient's tibia such that a predetermined gap is defined between the patient's tibia and the femoral cutting block. The method also includes rotating a distal end of the offset guide about a longitudinal axis extending through the intramedullary orthopaedic surgical instrument to determine an offset orientation for a prosthetic femoral component. Rotating the distal end of the offset guide includes adjusting a distance between the patient's tibia and the patient's femur.

In some embodiments, the method may require attaching an offset indicator to the distal end of the offset guide. Rotating the distal end of the offset guide may require rotating the offset indicator about a second longitudinal axis extending parallel to, and spaced apart from, the longitudinal axis extending through the intramedullary orthopaedic surgical instrument. In some embodiments securing the intramedullary orthopaedic surgical instrument to the offset guide may require positioning a triangular-shaped connector of the offset guide into a plurality of slots defined in an inner surface of the intramedullary orthopaedic surgical instrument, and engaging a sleeve of the offset guide with the intramedullary orthopaedic surgical instrument to secure the intramedullary orthopaedic surgical instrument to offset guide. In some embodiments, the inner surface of the intramedullary orthopaedic surgical instrument may be threaded and engaging the sleeve of the offset guide with the intramedullary orthopaedic surgical instrument may require engaging a threaded outer surface of the sleeve with the inner surface of the intramedullary orthopaedic surgical instrument. In some embodiments, the method may require securing a stem stabilizer to a stem trial to form the intramedullary orthopaedic surgical instrument.

BRIEF DESCRIPTION OF THE DRAWINGS

The detailed description particularly refers to the following figures, in which.

DETAILED DESCRIPTION OF THE DRAWINGS

Figure 1:
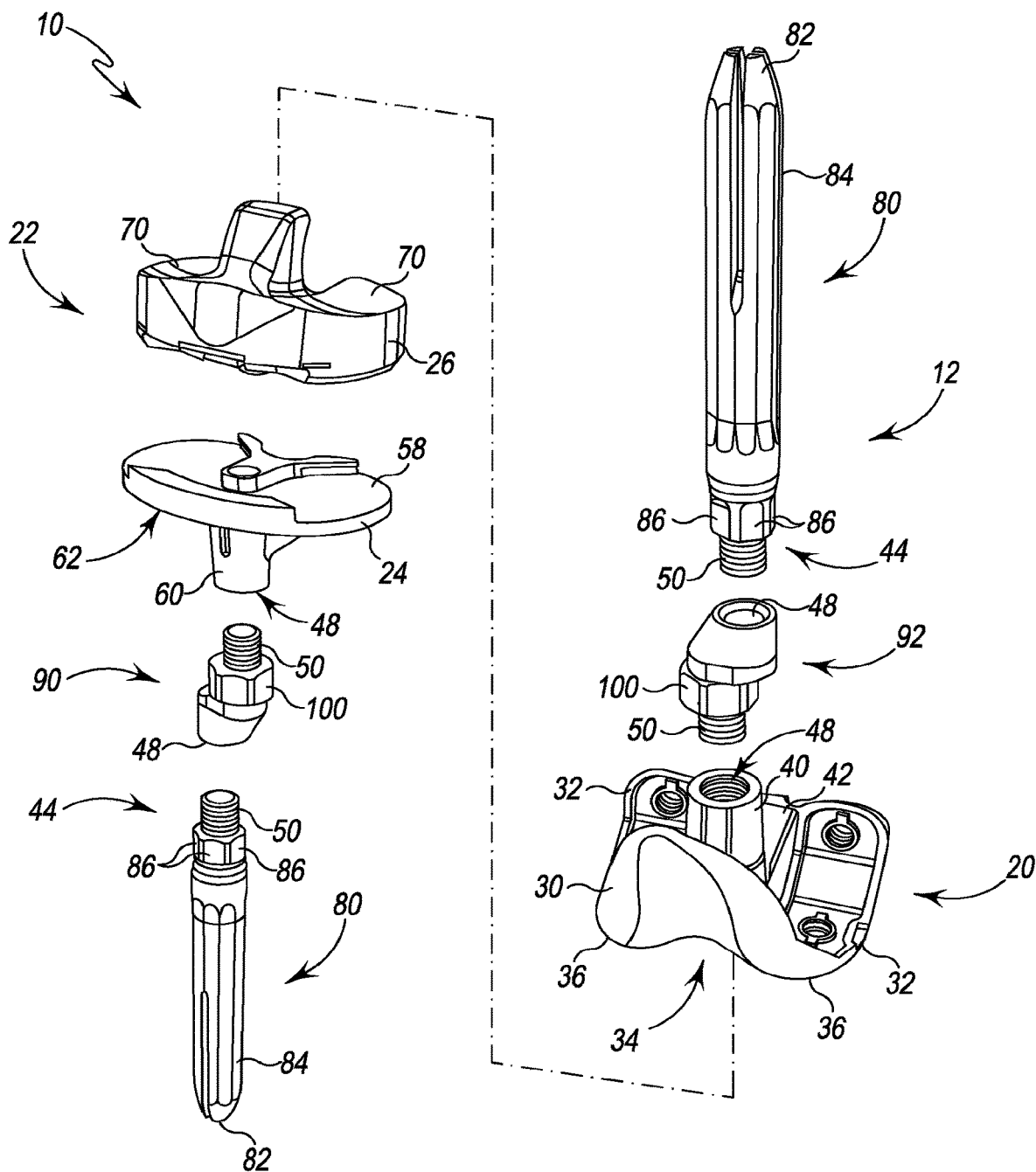
FIG. 1 is an exploded perspective view of prosthetic components of an orthopaedic joint replacement system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

The exemplary embodiments of the present disclosure are described and illustrated below to encompass prosthetic knee joints and knee joint components, as well as methods of implanting and reconstructing knee joints. It will also be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Referring now to FIG. 1, the orthopaedic joint replacement system 10 includes a number of orthopaedic prosthetic components 12 and a number of orthopaedic surgical instruments 14 (see, for example, FIG. 2) for use in preparing the bone to receive one or more of the prosthetic components 12. What is meant herein by the term "orthopaedic surgical instrument" or "orthopaedic surgical instrument system" is a surgical tool for use by a surgeon in performing an orthopaedic surgical procedure. As such, it should be appreciated that, as used herein, the terms "orthopaedic surgical instrument" and "orthopaedic surgical instruments" are distinct from orthopaedic prosthetic components or implants, such as those shown in FIG. 1.

The prosthetic components 12 of the system 10 include a prosthetic femoral component 20 configured to be secured to a surgically-prepared distal end of a patient's femur and a prosthetic tibial component 22 configured to be secured to a surgically-prepared proximal end of the patient's tibia. In the illustrative embodiment, the tibial component 22 includes a tibial tray 24 and a prosthetic insert 26 configured to engage the femoral component 20 after implantation into a patient's knee. It should be appreciated that the system 10 may include a number of components 12 corresponding to patients having bones of varying sizes. In that way, a surgeon will be able to select the components and other instruments that most-closely match the patient's bony anatomy.

As shown in FIG. 1, the femoral component 20 includes an anterior flange 30 and a pair of condyles 32 extending away from the flange 30. A notch 34, commonly called an intra-condylar notch, is defined between the condyles 32. The condyles 32 define articulation surfaces 36 configured to engage corresponding articulation surfaces 70 of the insert 26. The femoral component 20 also includes an elongated stem post 40, which extends superiorly away from its backside surface 42. As described in greater detail below, the femoral stem post 40 is configured to receive one of a number of different stem components 44. In the illustrative embodiment, a threaded bore 48, which is sized to receive a corresponding threaded shaft 50 of a stem component 44, is defined in the stem post 40.

The tibial tray 24 is configured to be implanted into a surgically-prepared end of a patient's proximal tibia (not shown). The tibial tray 24 includes a platform 58 having an elongated stem post 60 extending inferiorly away from its inferior surface 62. The elongated tibial stem post 60 is configured to receive one of a number of different stem components 44. Specifically, as can be seen in FIG. 1, a threaded bore 48, which is sized to receive a corresponding threaded shaft 50 of a stem component 44, is defined in the stem post 60.

The insert 26 is securable to the tibial tray 24. In particular, the insert 26 may be snap-fit to the tibial tray 24. In such a way, the insert 26 is fixed relative to the tibial tray 24 (i.e., it is not rotatable or moveable in the anterior/posterior or medial/lateral directions). Although, in other embodiments, the tibial tray may be secured in a manner that allows it to rotate relative to the tibial tray 24.

The insert 26 includes lateral and medial articulation surfaces 70. The surfaces 70 are configured to articulate with the corresponding articulation surfaces 36 of the femoral component 20. Specifically, the femoral component 20 is configured to be implanted into a surgically-prepared distal end of the patient's femur (not shown), and is configured to emulate the configuration of the patient's natural femoral condyles. As such, the articulation surfaces 36 of the femoral component 20 are configured (e.g., curved) in a manner which mimics the condyles of the natural femur.

As shown in FIG. 1, the stem components 44 of the system 10 include elongated stems 80, which are configured to be attached to either of the components 20, 22. Each elongated stem 80 extends from the threaded shaft 50 at one end to a pointed tip 82 at the opposite end. Each stem also includes a ribbed outer surface 84 extending from the pointed tip 82 toward the threaded shaft 50. A plurality of substantially planar surfaces 86 are positioned around the outer circumference of the stem 80 adjacent to the shaft 50. The surfaces 86 are sized and positioned to receive the end of a wrench or other installation tool so that the stem 80 may be rotated into tight engagement with one of the threaded bores 48.

In the illustrative embodiment, the prosthetic components 12 also include a plurality of offset adapters 90, 92 configured to be attached to the components 20, 22. As shown in FIG. 1, the adapter 90 is configured to offset the longitudinal axis of the elongated stem 80 from the longitudinal axis of the stem post 60 of the tibial tray 24 by a predetermined amount. Similarly, the adapter 92 is configured offset the longitudinal axis of the elongated stem 80 from the longitudinal axis of the stem post 40 of the femoral component 20. Each of the adapters 90, 92 includes a threaded shaft 50 configured to be received in the threaded bore 48 of either of the components 20, 22. Each of the adapters 90, 92 also includes a threaded bore 48 at its opposite end, which is sized to receive a threaded shaft 50 of one of the elongated stems 80. In the illustrative embodiment, a locking nut 100 is positioned on the threaded shaft 50 of each of the adapters 90, 92. The locking nut 100 may be typed against the surface of the stem post of each component to secure the adapter thereto.

The components of the knee prosthesis 10 that engage the natural bone, such as the femoral component 20, the tibial tray 24, and the stem components 44, may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel. Such a metallic components may also be coated with a surface treatment, such as hydroxyapatite, to enhance biocompatibility. Moreover, the surfaces of the metallic components that engage the natural bone may be textured to facilitate securing the components to the bone. Such surfaces may also be porous coated to promote bone ingrowth for permanent fixation.

The insert 26 may be constructed with a material that allows for smooth articulation between the insert 26 and the femoral component 20, such as a polymeric material. One such polymeric material is polyethylene such as ultrahigh molecular weight polyethylene (UHMWPE).

Figure 2:
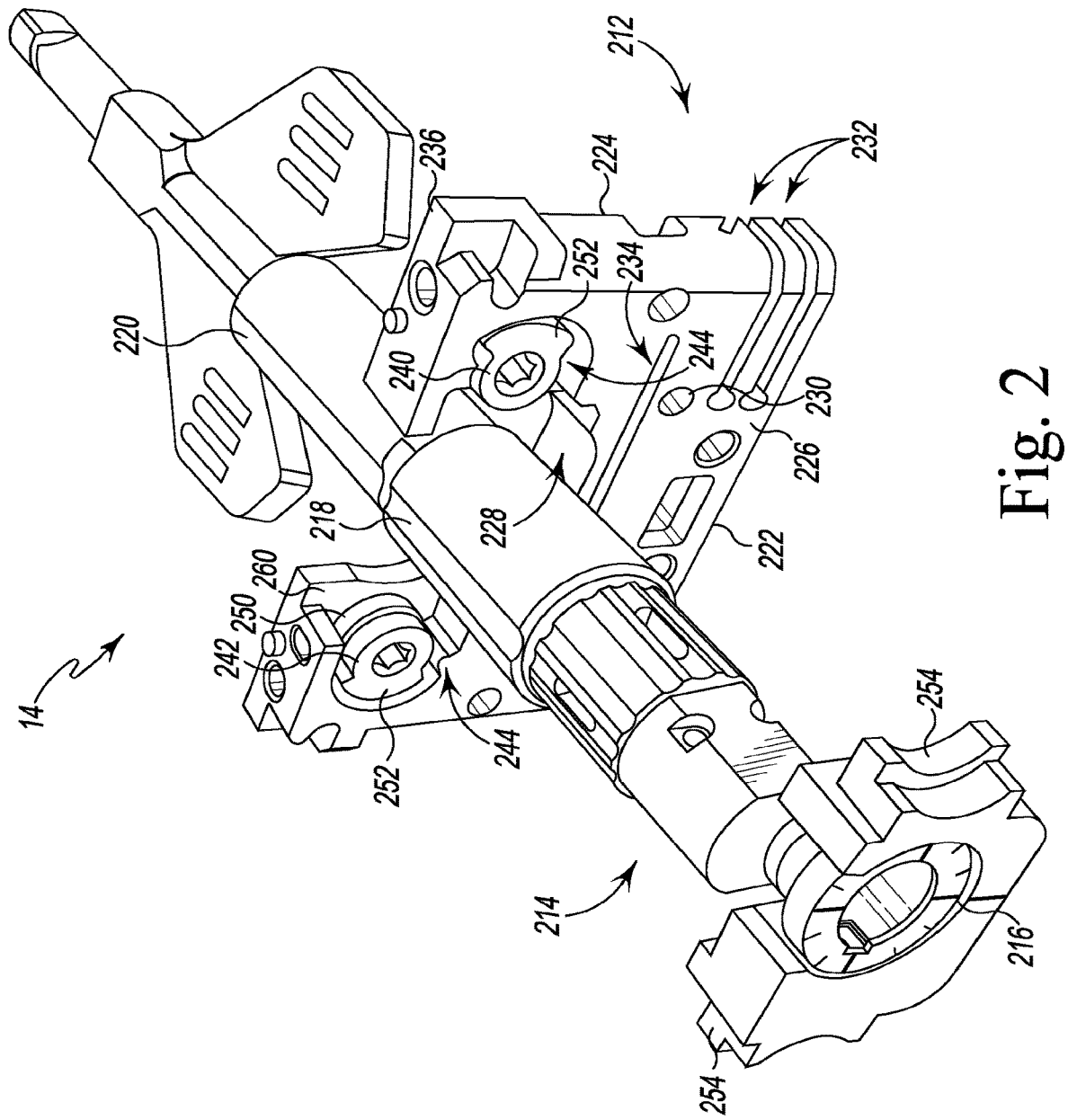
FIG. 2 is an exploded perspective view of a femoral cutting guide assembly of the orthopaedic joint replacement system.

Referring now to FIG. 2, the system 10 includes a number of surgical instruments 14. The surgical instruments include a base cutting block 212 configured for use on a femur of a patient and an offset guide assembly 214 configured to be secured to the base cutting block 212. In the illustrative embodiment, the offset guide assembly is an "intramedullary orthopedic surgical instrument," which is a surgical tool configured to be at least partially positioned in the medullary canal of the patient's femur during the orthopedic surgical procedure. As shown in FIG. 2, the offset guide assembly 214 includes an offset guide 216 and a stem stabilizer 218 configured to be attached to a stem trial 220 (see FIG. 5). It should be appreciated that an assembly including the offset guide 216 and the stem stabilizer 218 without the stem trial may be an intramedullary orthopedic surgical instrument; similarly, an assembly including the stem stabilizer 218 and the stem trial 220 may be an intramedullary orthopedic surgical instrument.

The base cutting block 212 includes a base plate 222, which is formed from a metallic material, such as, for example, a stainless steel or cobalt chrome alloy. The base plate includes a distal surface 224 and a proximal surface 226 that is positioned opposite the distal surface. A passageway 228 extends through the surfaces 224, 226, and the passageway 228 is sized to permit the passage of the offset guide assembly 214, as shown in FIG. 2. The base cutting block 212 includes a number of fixation pin guide holes 230, which are sized to receive fixation pins 262 to secure the base cutting block to the patient's femur.

The base cutting block 212 includes a number of cutting guides 232, which may be used during the orthopedic surgical procedure to resect a portion of a patient's femur. In the illustrative embodiment, each of the cutting guides 232 is a posterior cutting guide for use in guiding the resection of a posterior surface of the patient's femur. The base cutting block 212 also includes a posterior chamfer cutting guide 234, which may be used to guide the resection of a posterior chamfer surface of the patient's femur. Each guide includes an elongated slot that is sized to receive a cutting saw blade of a surgical saw or other device. The base cutting block 212 also includes a mounting platform 236, which is configured to receive modular cutting guide blocks that may be selectively secured to the base cutting block 212, as described in greater detail below.

Figure 4:
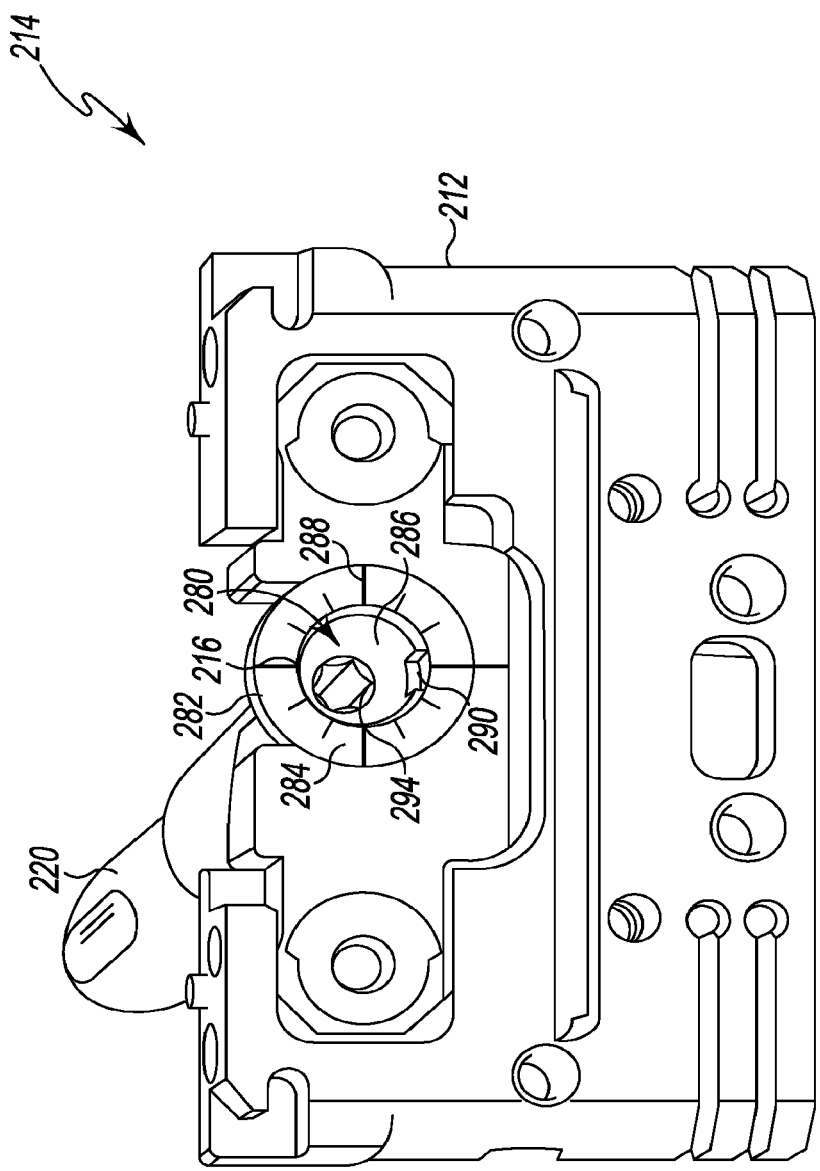
FIG. 4 is a distal perspective view of the femoral cutting guide assembly of FIG. 2 with the stem trial.

As described above, the offset guide assembly 214 may be secured to the base cutting block 212. As shown in FIG. 2, the base cutting block 212 includes a pair of locking tabs 240, 242 that are pivotally coupled to the base plate 222. Each of the tabs 240, 242 is positioned in an aperture 244 positioned on each side of the passageway 228. The tabs 240, 242 are coupled to the base plate 222 via pivot joint 250, which permits the locking tabs 240, 242 to rotate between a locked position and an unlocked position. In the unlocked position, an ear 252 of the locking tab faces away from the passageway 228, as shown in FIG. 2. In the locked position, the ear 252 faces toward the passageway 228. When the offset guide 216 is positioned as shown in FIG. 4, the ears 252 of the locking tabs 240, 242 are positioned over retaining flanges 254 of the offset guide 216. In that way, the retaining flanges 254 are captured between the locking tabs 240, 242 and a bottom wall 260 of the plate 222.

Figure 3:
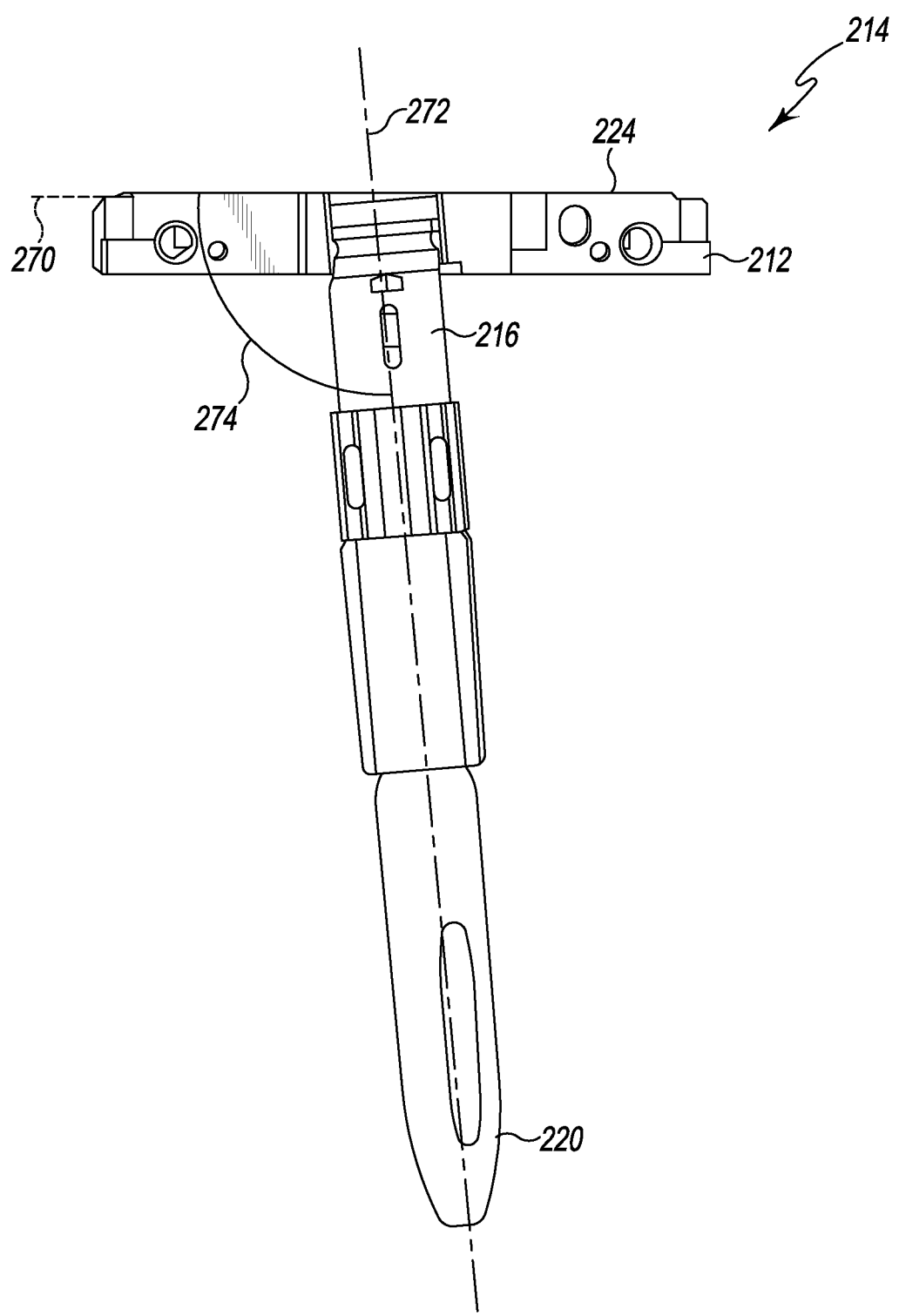
FIG. 3 is a side elevation view of femoral cutting guide assembly of FIG. 2 with the stem trial.

Referring now to FIG. 3, the distal surface 224 of the cutting block 212 defines an imaginary plane 270, and a longitudinal axis 272 extends along the offset guide assembly 214 through the stem trial 220. In the illustrative embodiment, the axis 272 corresponds to the longitudinal axis of the elongated stem 80 of the femoral prosthetic assembly. An oblique angle 274 is defined between the axis 272 and the imaginary plane 270, which corresponds to the angle between the elongated stem 80 and the femoral component 20 in the femoral prosthetic assembly.

As shown in FIG. 4, the offset guide assembly 214 includes an aperture 280 that is formed at its distal end 282. The aperture 280 extends inwardly from an annular surface 284 to a bottom surface 286. The annular surface 284 includes a number of indicia 288, and, as shown in FIG. 3, also extends at an oblique angle relative to the distal surface 224 of the cutting block 212, orthogonal to the longitudinal axis 272. In the illustrative embodiment, the indicia 288 include lines etched in the surface 284. As described in greater detail below, the indicia 288 may be used to provide the surgeon with an indication of the offset orientation during a surgical procedure. An alignment groove 290, which orients an offset indicator 292 (see FIG. 8), is defined in the annular surface 284. The offset guide assembly 214 also includes a socket 294 that is defined in the bottom surface 286 of the aperture 280. The socket 294 is sized to receive a hex end of a driver 296 (see FIG. 11), as described in greater detail below.

Figure 5:
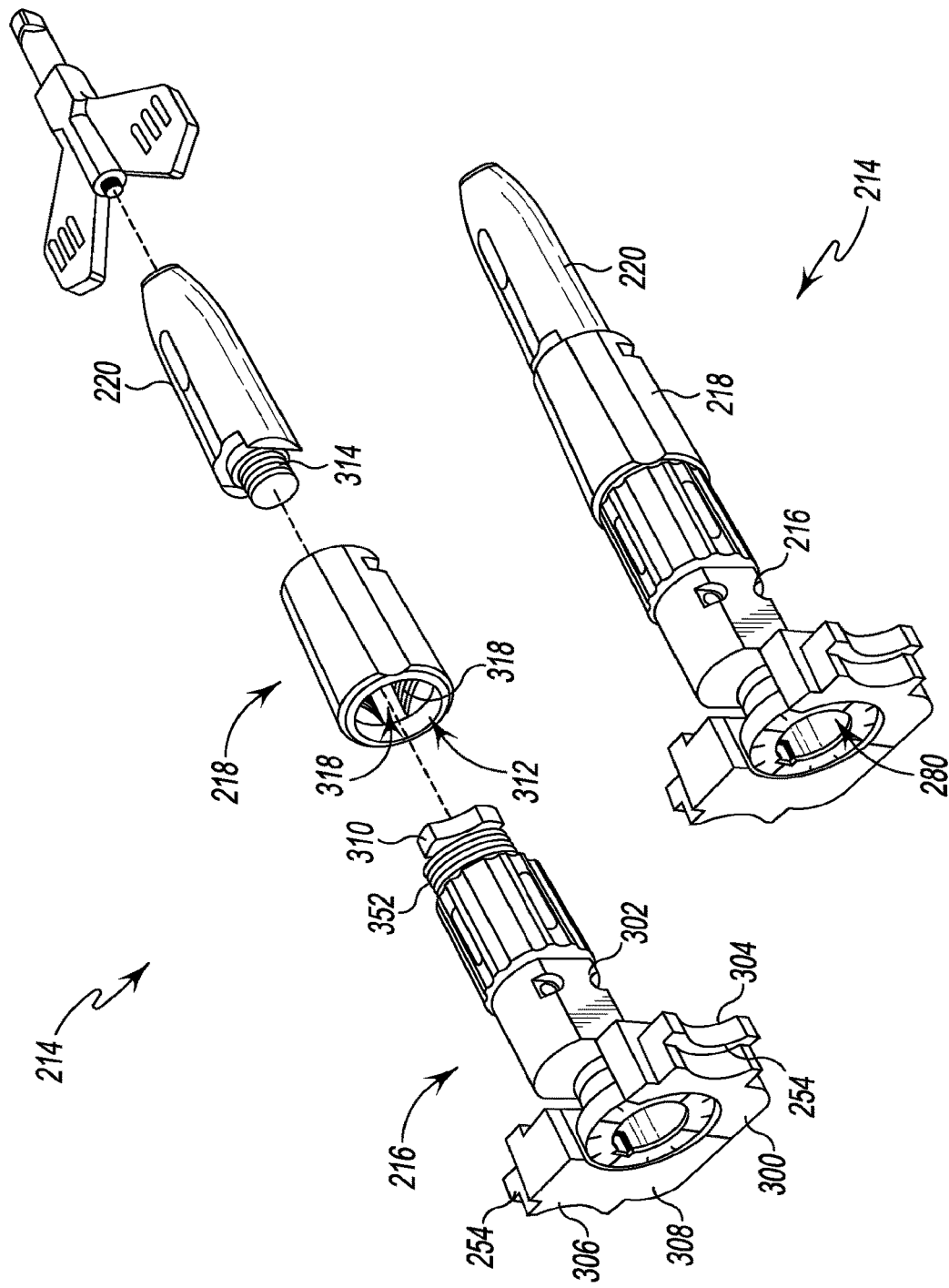
FIG. 5 illustrates a perspective view and exploded perspective view the femoral cutting guide assembly and the stem trial of FIG. 3.

Referring now to FIG. 5, the offset guide assembly 214 includes the offset guide 216, the stem stabilizer 218, which may be selectively attached to the offset guide 216, and one of a number of stem trials 220, which vary in length and diameter and may be selectively attached to the stabilizer 218. In the illustrative embodiment, the guide 216, stabilizer 218, and stem trial 220 are formed from metallic materials, such as, for example stainless steel or cobalt chrome alloy. The offset guide 216 includes a mounting bracket 300 and an adapter body 302 that is pivotally coupled to the mounting bracket 300. The mounting bracket 300 includes the retaining flanges 254, which are positioned at each of its ends 304, 306 and are sized to receive the ears 252 of the locking tabs 240, 242. The mounting bracket 300 also includes a distal surface 308 that extends parallel to the distal surface 224 of the cutting block 212 when the offset guide assembly 214 is attached to the cutting block 212.

Figure 21:
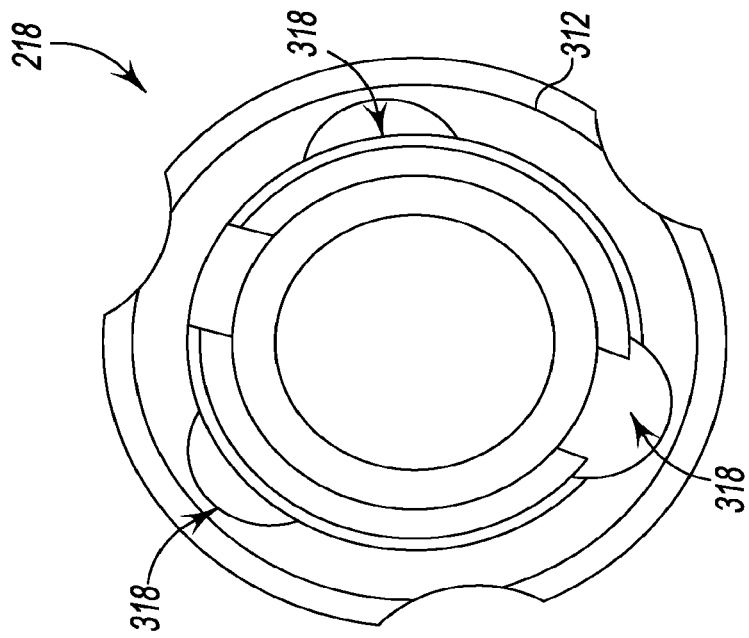
FIG. 21 is an elevation view of the stem stabilizer of FIG. 20.
Figure 20:
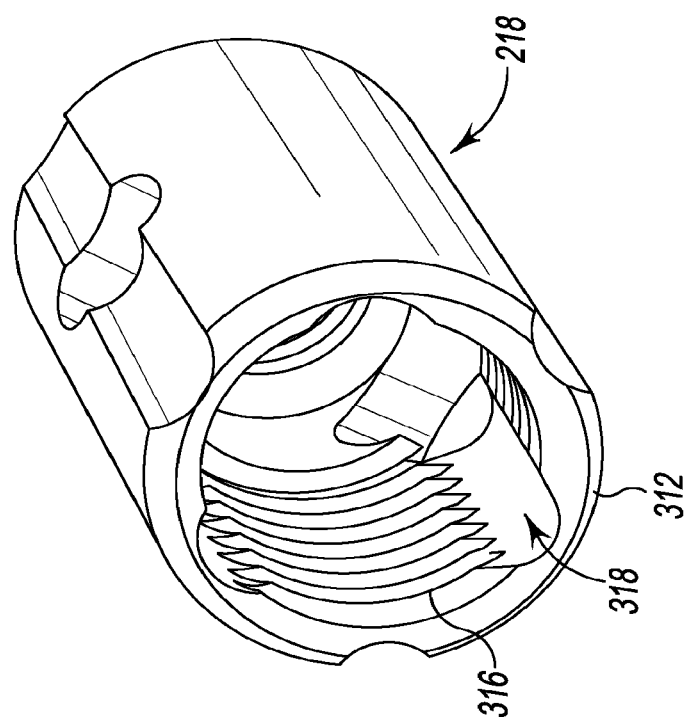
FIG. 20 is a perspective view of a stem stabilizer of FIG. 4.

The offset guide 216 has a proximal end 310 that includes a connector having a triangular shape. The stabilizer 218 has a distal opening 312 that is sized to receive the proximal end 310. As shown in FIG. 5 and in greater detail in FIGS. 20-21, the stabilizer 218 includes an inner wall 316 that extends inwardly from the distal opening 312. The inner wall 316 is threaded and has a plurality of longitudinal slots 318 defined in the threads. Each slot 318 is sized to receive a tip of the triangular-shaped connector 310.

To assemble the offset guide 216 to the stem stabilizer 218, the surgeon may locate the proximal end 310 in the opening 312 and tighten the threads of the offset guide 216, as described in greater detail below. The stabilizer 218 also has a threaded proximal opening (not shown) that is sized to receive the threaded distal end 314 of the stem trial 220.

Figure 6:
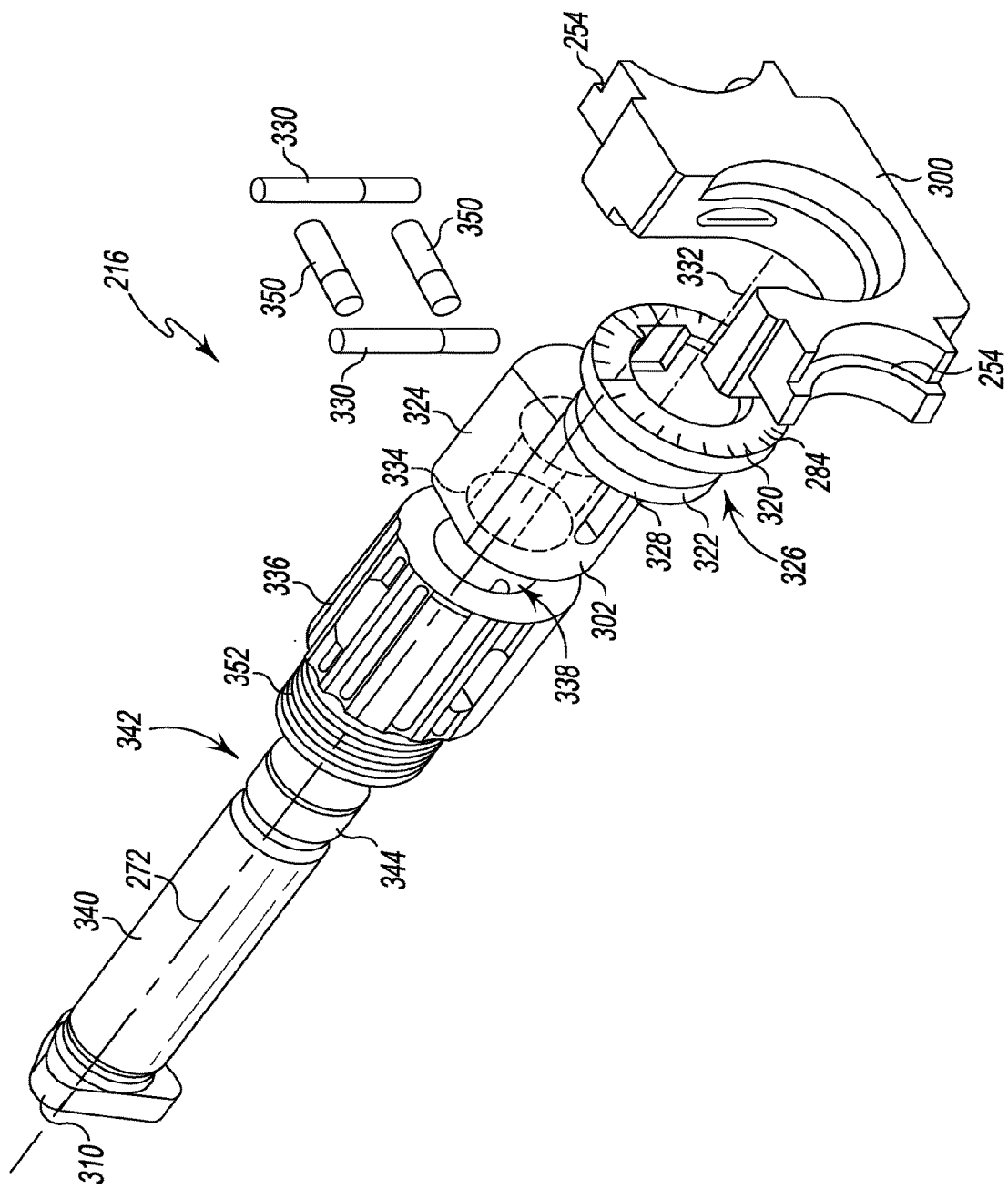
FIG. 6 is an exploded perspective view of the femoral offset guide of FIG. 3.
Figure 7:
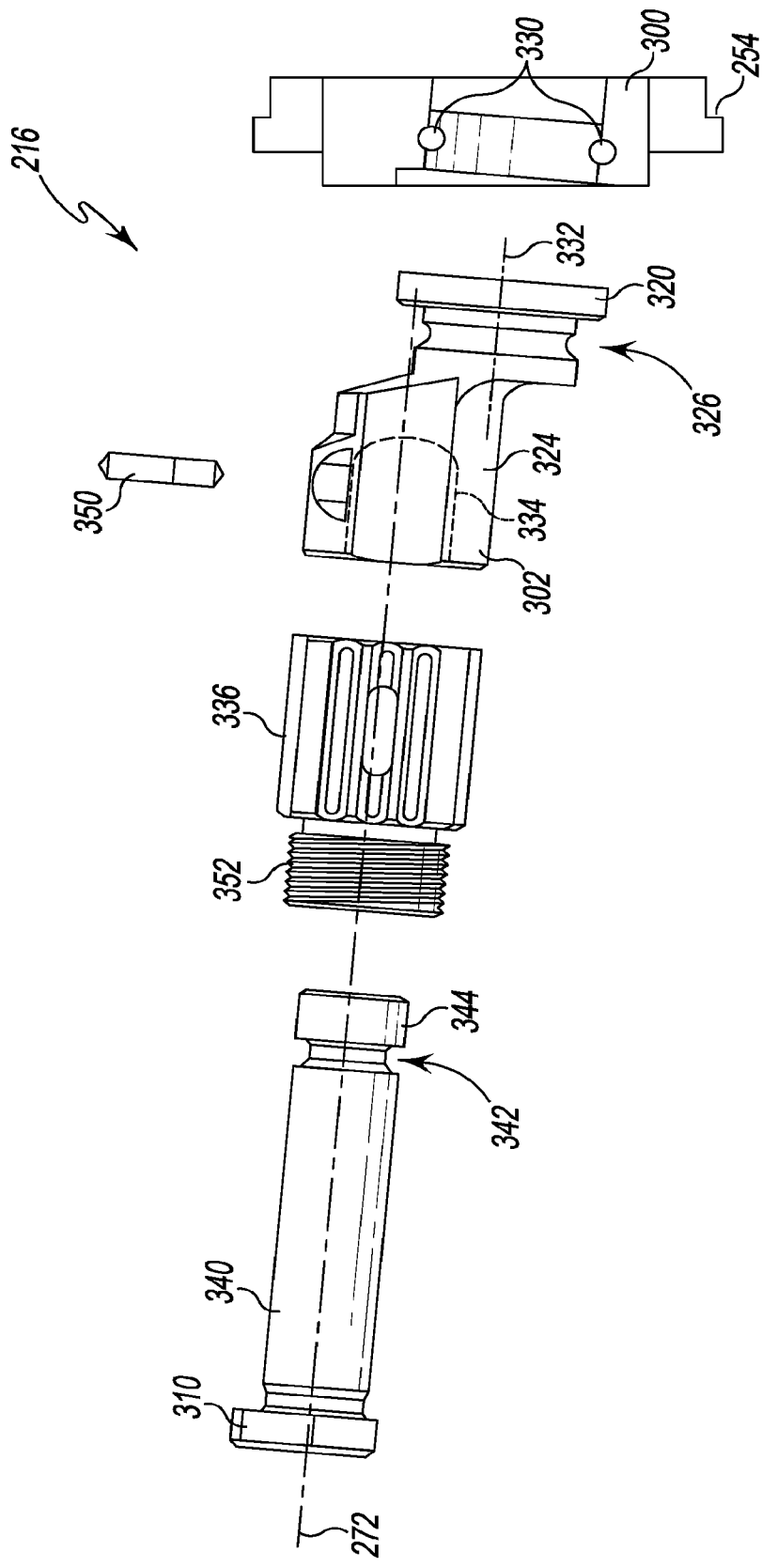
FIG. 7 is an exploded elevation view of the femoral offset guide of FIG. 6.

Referring now to FIGS. 6-7, the adapter body 302 of the offset guide 216 includes the annular surface 284 described above. The annular surface 284 is included on a head plate 320 of the adaptor body 302. A post 322 extends away from the head plate 320, and the adapter body 302 includes a lower shell 324 that is connected to, but offset from, the post 322. The post 322 includes an annular groove 326 that is defined in its outer surface 328. In the illustrative embodiment, the offset guide 216 includes a pair of pins 330 that extend through the mounting bracket 300 and are positioned in the annular groove 326 to secure the adapter body 302 to the mounting bracket 300. The smooth outer surfaces of the pins 330 permit the cylindrical post 322 to rotate about its longitudinal axis 332 relative to the mounting bracket 300. As shown in FIG. 6, the longitudinal axis 332 of the post 322 is offset from, and extends parallel to, the longitudinal axis 272 of the offset guide assembly 214. It should be appreciated that the same oblique angle 274 described above in regard to FIG. 3 is defined between the longitudinal axis 332 and the imaginary plane 270.

The lower shell 324 of the adapter body 302 has a distal-facing aperture 334. The offset guide 216 includes an intermediate housing or sleeve 336 that is positioned below the lower shell 324. The housing 336 has a passageway 338 that is aligned with the aperture 334 of the lower shell 324. As shown in FIGS. 6-7, the triangular-shaped proximal end 310 is attached to an elongated shaft 340 that is sized to be positioned in the passageway 338 and the aperture 334. The elongated shaft 340 has an annular groove 342 positioned adjacent to its distal end 344. A pair of pins 350 extend through the lower shell 324 and into the annular groove 342. The smooth outer surfaces of the pins 350 permit the elongated shaft 340 (and hence the proximal end 310) to rotate about the longitudinal axis 272 relative to the adapter body 302. The housing 336 and the elongated shaft 340 are configured to permit limited axial movement along the longitudinal axis 272 relative to the mounting bracket 300.

The sleeve 336 also includes a threaded outer surface 352 that positioned adjacent to the connector end 310 of the elongated shaft 340. As described above, the threaded outer surface 352 of the guide 216 is configured to engage the threaded inner wall 316 of the stabilizer 316 to secure the stabilizer 316 on the guide 216. As described above, the stabilizer 316 is first positioned on the connector end 310 of the guide 216 with the tips of connector positioned in the elongated slots 318 of the stabilizer 218. The sleeve 336 is then moved along the axis 272 toward the connector end 310 to engage its threaded outer surface 352 with the threaded inner wall 316 of the stabilizer 316. The sleeve 336 may then be threaded into the stabilizer 218 to secure the parts together.

Figure 8:
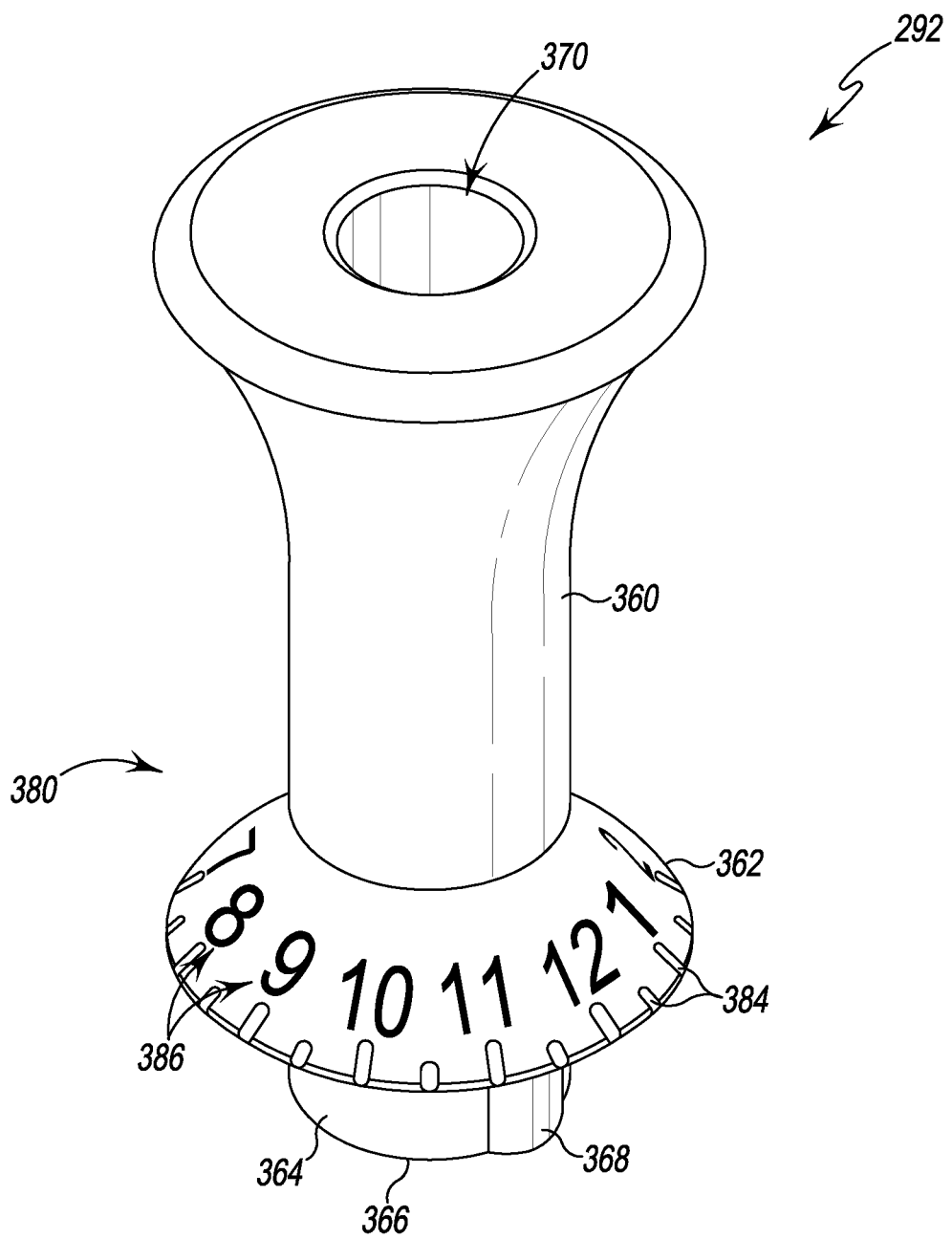
FIG. 8 is a perspective view of an offset indicator of orthopaedic joint replacement system.

Referring now to FIG. 8, the offset indicator 292 includes a central post 360 that is connected to a conical flange 362. The post 360 includes a plug 364 that extends downwardly from the flange 362 to the end 366 of the indicator 292. The plug 364 is sized to be positioned in the distal aperture 280 of the offset guide assembly 214 and includes an alignment tab 368 that is sized to be received in the groove 290 defined in the offset guide assembly 214.

The offset indicator 292 has a passageway 370 that extends through the post 360. The passageway 370 is sized to receive the hex end of the driver 296. In the illustrative embodiment, the passageway 370 is defined by a smooth cylindrical surface 372 such that the offset indicator 292 does not engage the driver 296 and rotate directly with it. Instead, the engagement between tab 368 of the indicator 292 and the groove 290 of the offset guide 216 causes the offset indicator to rotate with the adaptor body 302 of the offset guide.

As shown in FIG. 8, the conical flange 362 has a plurality of indicia 380 located on its upper surface 382. In the illustrative embodiment, the indicia 380 include etched lines 384 and numbers 386 associated with each etched line 384. The numbers 386 correspond to predetermined offset orientations of the offset adaptor 92 for the femoral component 20. When an etched line 384 of the indicator 292 is aligned with an etched mark 390 on the mounting bracket 300 (see FIGS. 12A and B), the surgeon identifies the number 386 associated with that line 384. The number is then used to set the final offset orientations of the offset adaptor 92. It should be appreciated that other indicia may be used to inform the surgeon of the offset orientation.

Figures 9, 9A:
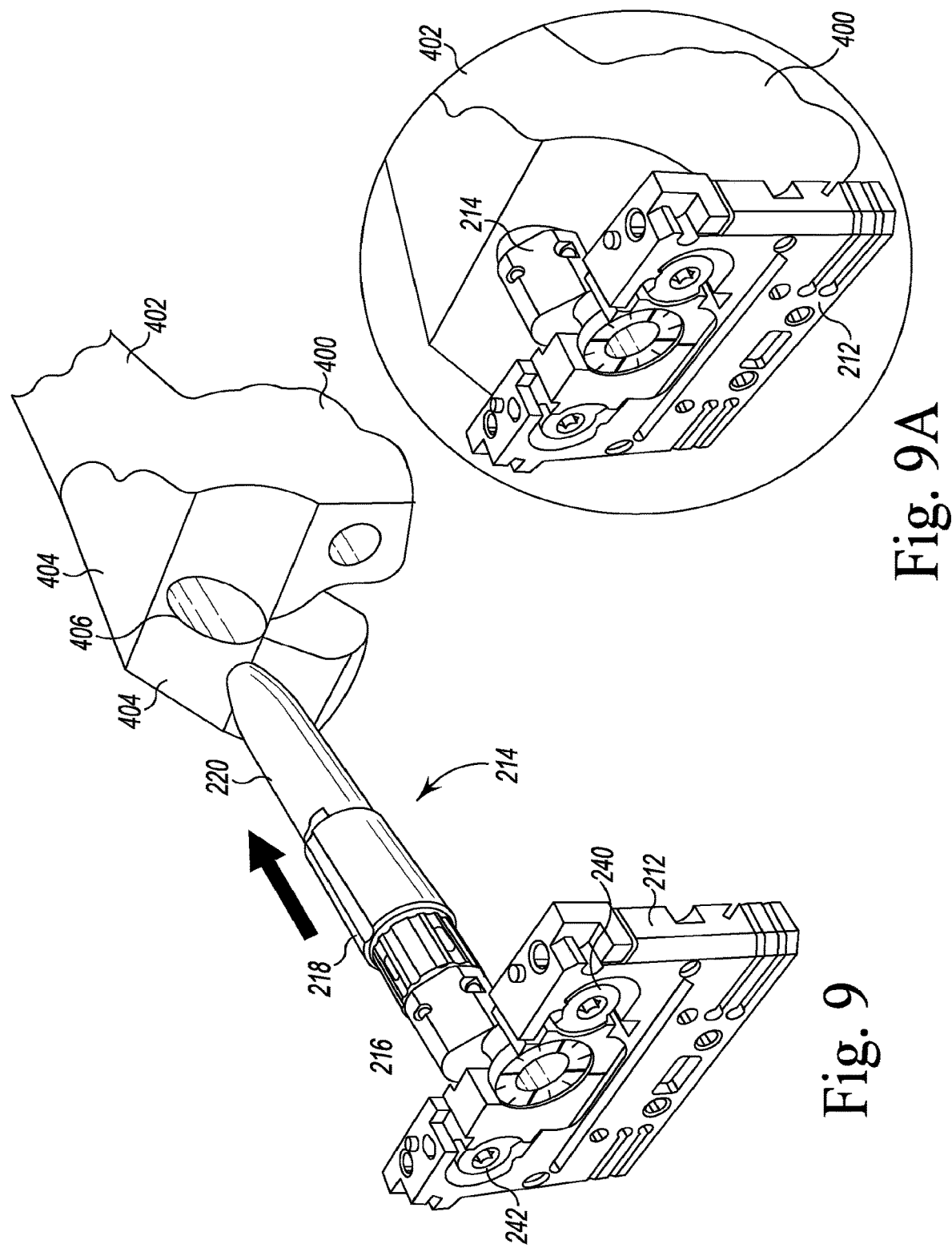
FIGS. 9-19 illustrate a number of steps of a surgical procedure utilizing the orthopaedic joint replacement system.

As described above, the instruments 14 may be used to surgically prepare a patient's femur to receive a prosthetic femoral component 20 and one of the stem components 44. In the illustrative embodiment, the instruments 14 may be used in a revision procedure in which a primary implant has been removed from a distal end of the patient's femur. As shown in FIG. 9, the distal end 400 of a patient's femur 402 in a revision procedure includes a plurality of surfaces 404 that had been previously-shaped to receive the primary implant. During a revision procedure, the surfaces 404 are resected to prepare the distal end 400 to receive the prosthetic femoral component 20. FIGS. 9-19 illustrate a number of exemplary steps of a procedure for surgically-preparing the distal end 400 during a revision procedure. It should be appreciated that any surgical procedure may include additional or fewer steps depending on the state of the patient's bony anatomy and the preferences of the surgeon.

Referring now to FIG. 9, the distal end 400 of the patient's femur 402 includes an opening 406 defined in one of the surfaces 404. The opening 406 permits the surgeon to access the intramedullary canal of the patient's femur 402. To resect the patient's bone, surgeon may begin by assembling the offset guide 216, a stem stabilizer 218, and a stem trial 220 to form the offset guide assembly 214 shown in FIG. 9. By utilizing the locking tabs 240, 242, the surgeon may attach the offset guide assembly 214 to the base cutting block 212.

With the offset guide assembly 214 attached to the base cutting block 212, surgeon may align the proximal tip of the stem trial 220 with the opening 406 in the patient's femur 402, as shown in FIG. 9. The surgeon may then advance the stem trial 220 into the opening 406, as indicated by arrow 410. The surgeon may continue to move the base cutting block 212 and the offset guide assembly 214 in the direction indicated by arrow 410 to position the base cutting block 212 in contact with the distal end 400 of the patient's femur 402, as shown in FIG. 9A. With the base cutting block 212 positioned as shown in FIG. 9A, the surgeon may place the knee joint in extension and evaluate the extension space.

Figure 10:
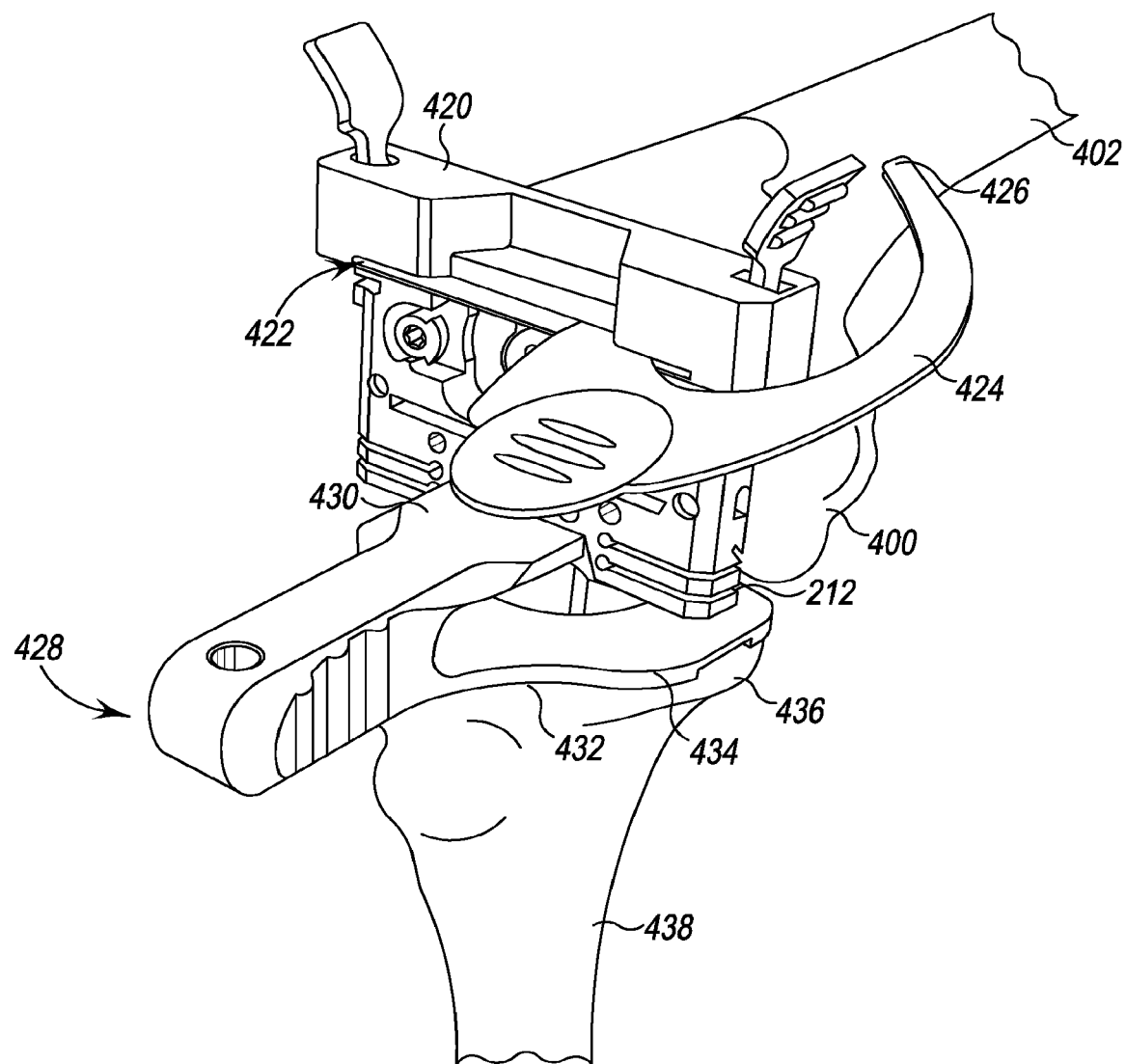

After returning the joint to flexion as shown in FIG. 10, the surgeon may attach an anterior cutting block 420 to the mounting platform 236 of the base cutting block 212. The anterior cutting block 420 includes a cutting guide 422 that is sized to receive a cutting blade of a surgical saw. To assess the balance of the knee joint, the surgeon may position alignment tool 424 in the cutting guide 422 such that a probe tip 426 of the tool 424 contacts the patient's femur 402. The alignment tool 424 may be used to assess the anterior resection performed using the anterior cutting block 420.

The surgeon may attach a balancing block 428 to the base cutting block 212, as shown in FIG. 10. The balancing block includes a handle and an upper arm 430 and lower arm 432 extending outwardly from the handle. The upper arm 430 is configured to be attached to the base cutting block 212, and the lower arm 432 includes a plate 434 sized to be positioned on a surgically-prepared proximal end 436 of a patient's tibia 438 or on a tibial base plate (if any) attached to the patient's tibia. As shown in FIG. 10, the upper arm 430 is spaced a predefined distance from the lower arm 432 such that the proximal end 436 of the patient's tibia 438 is spaced a predetermined distance from the cutting block 212.

Figure 11:
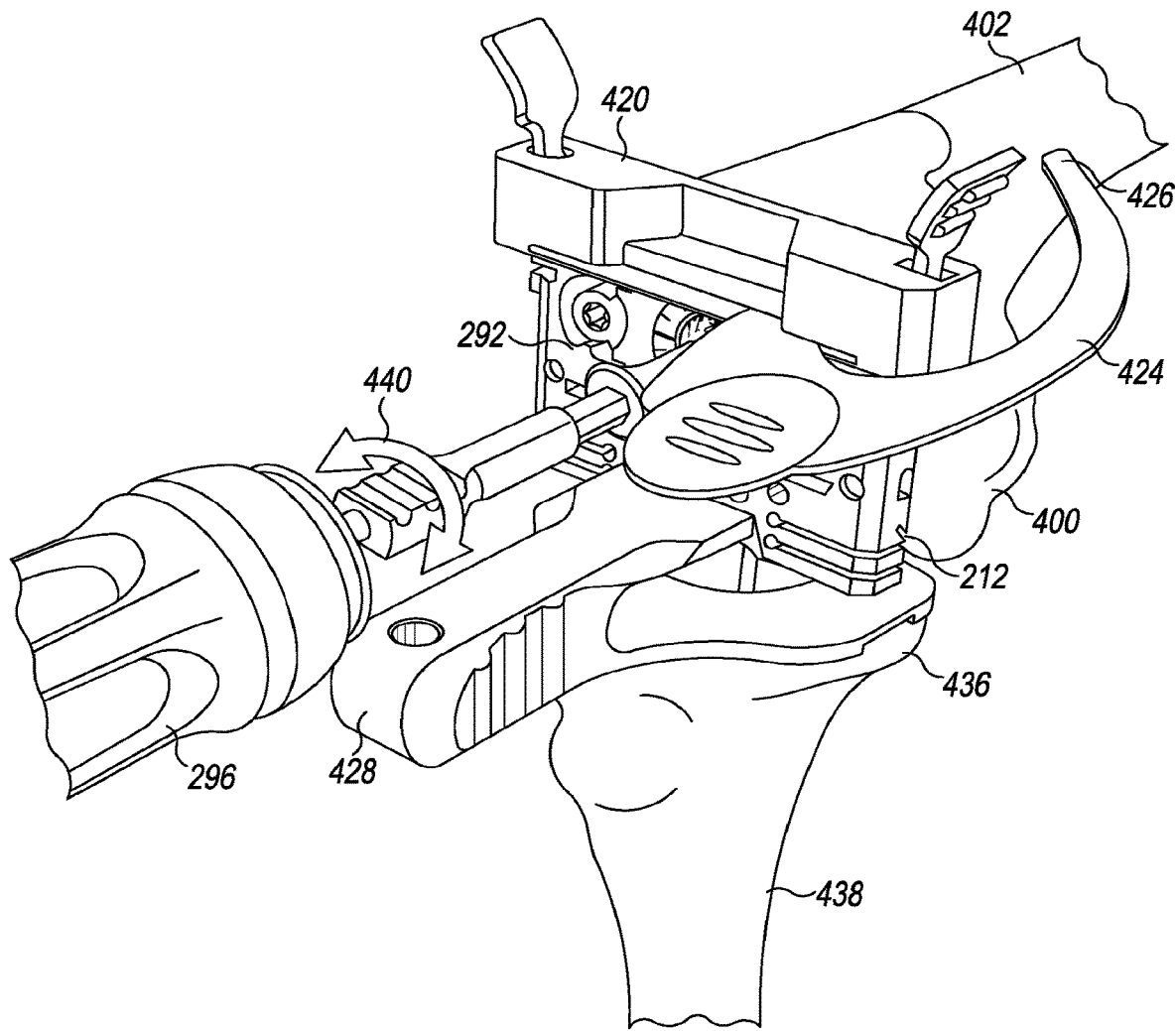

As shown in FIG. 11, the surgeon may attach the offset indicator 292 to a driver 296 and then advance the offset indicator 292 into the aperture 280 defined in the offset guide assembly 214. As described above, the passageway 370 of the offset indicator 292 is sized to permit the passage of the hex head of the driver 296, thereby allowing the hex head to enter the socket 294 defined at the base of the aperture 280. The surgeon may then rotate the driver 296 as indicated by arrows 440.

The engagement between the driver 296 and the offset guide 216 causes the adapter body 302 to rotate about its axis 332 with the driver 296. As the adapter body 302 rotates, the engagement between the stem stabilizer 218 and the patient's femur 402 causes the adapter body 302 and the cutting block 212 to rotate about the axis 272. This combined rotation causes the cutting block 212 to be repositioned on the distal end 400 of the patient's femur 402. As the cutting block 212 rotates relative to the distal end 400 of the patient's femur 402, the block 428 maintains the cutting block 212 in position relative to the tibia 438, and the distance (and position) between the distal end 400 of the patient's femur 402 and the proximal end 436 is adjusted.

Figure 12A:
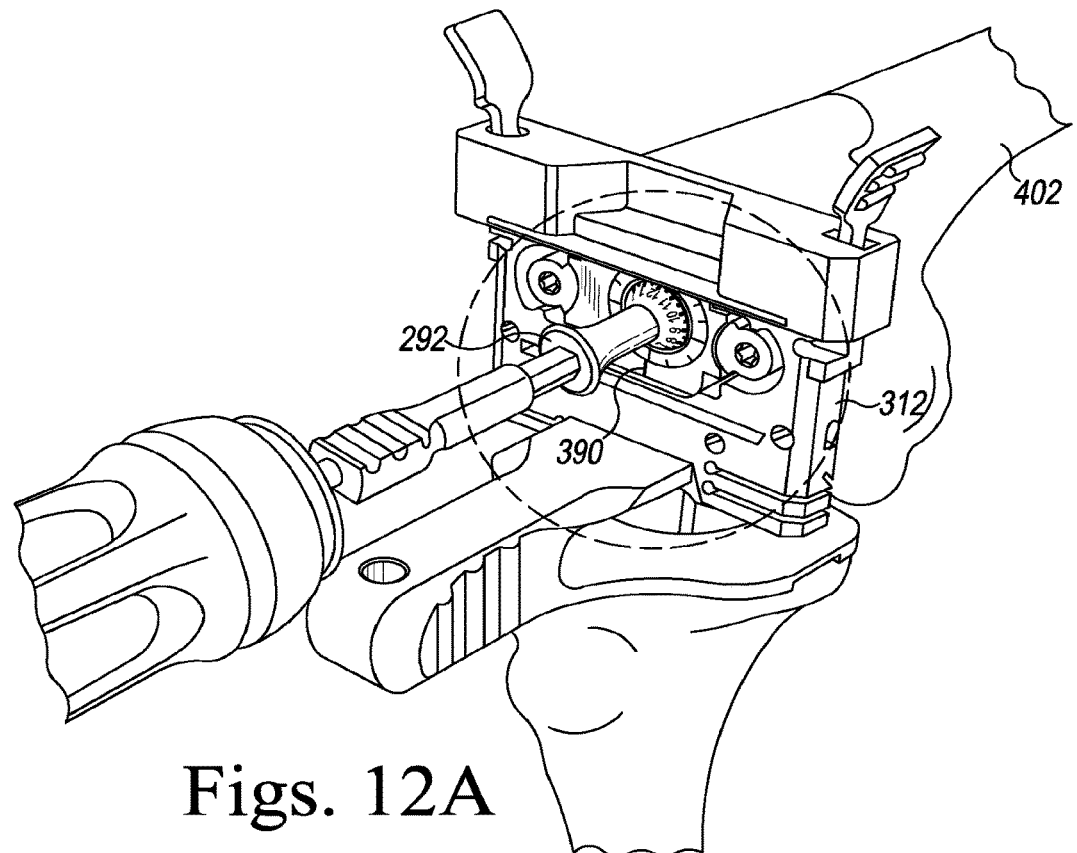
Figure 12B:
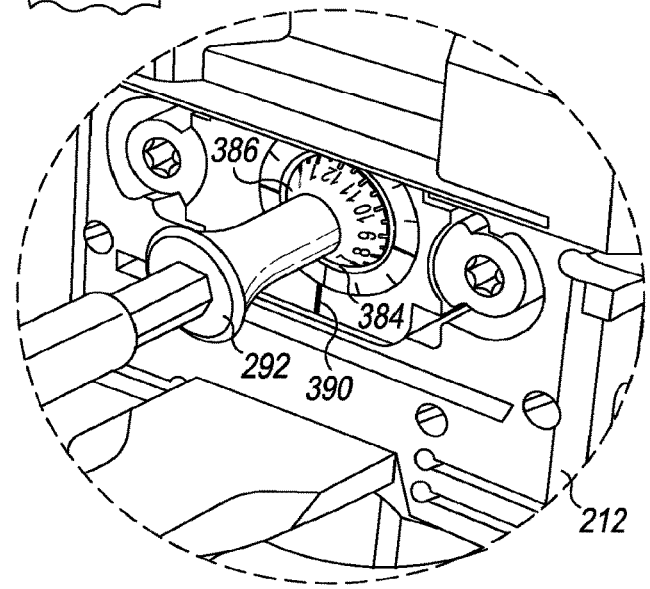

With the balancing block 428 still attached to the cutting block 212, the surgeon may continue to assess ligament tension while at the same time determining the offset orientation. When the desired offset has been achieved, the surgeon may insert one or more fixation pins 450 (see FIG. 13) into the patient's femur 402 through the guide holes 230 defined in the cutting block 212. As shown in FIGS. 12A and 12B, the surgeon may note the preliminary offset position from the alignment of the etched line 384 and associated number 386 on the offset indicator 292 with the etched mark 390 on the mounting bracket 300.

Figure 18:
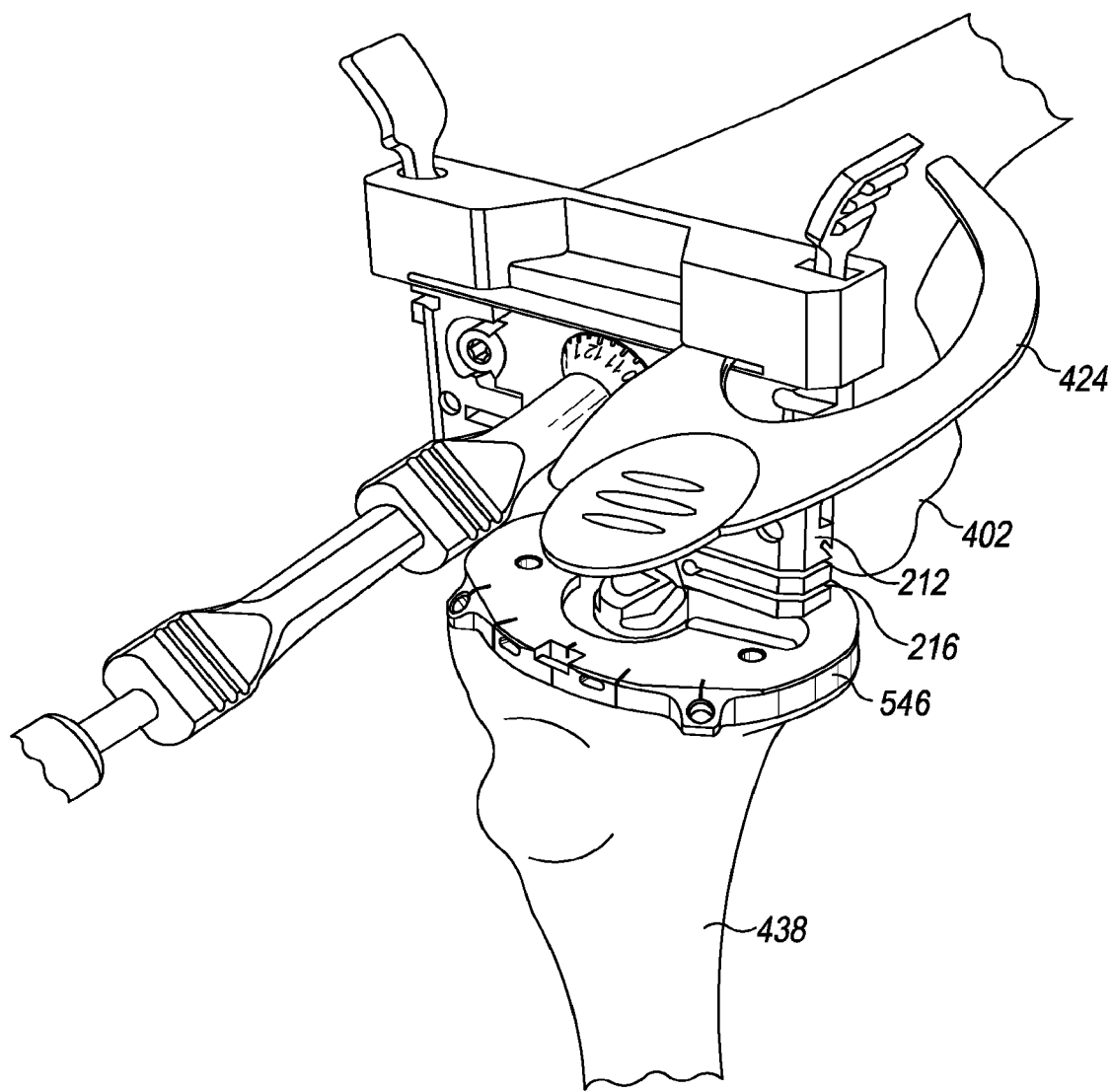
Figure 19:
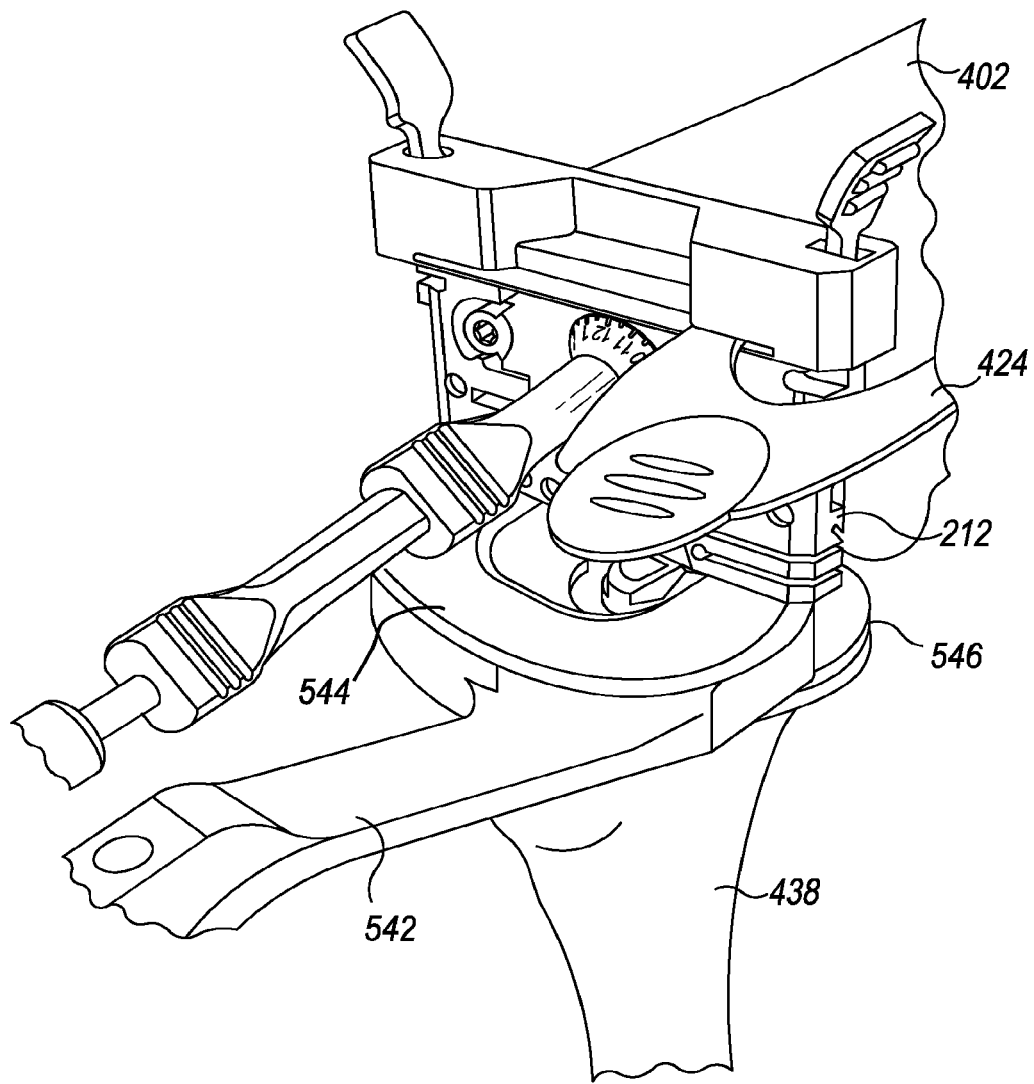

Referring now to FIGS. 18-19, a surgeon may evaluate ligament tension during the surgical procedure using other methods. For example, as shown in FIG. 18, the surgeon may utilize visual landmarks on the patient's femur 402 and tibia 438 to determine the desired offset orientation. As shown in FIG. 19 the surgeon may utilize a spacer instrument 542, which includes a distal end 544 configured to engage the cutting block 212 and the patient's tibia 438 (or tibial base plate 546) to evaluate ligament tension and set the offset orientation.

Figure 13:
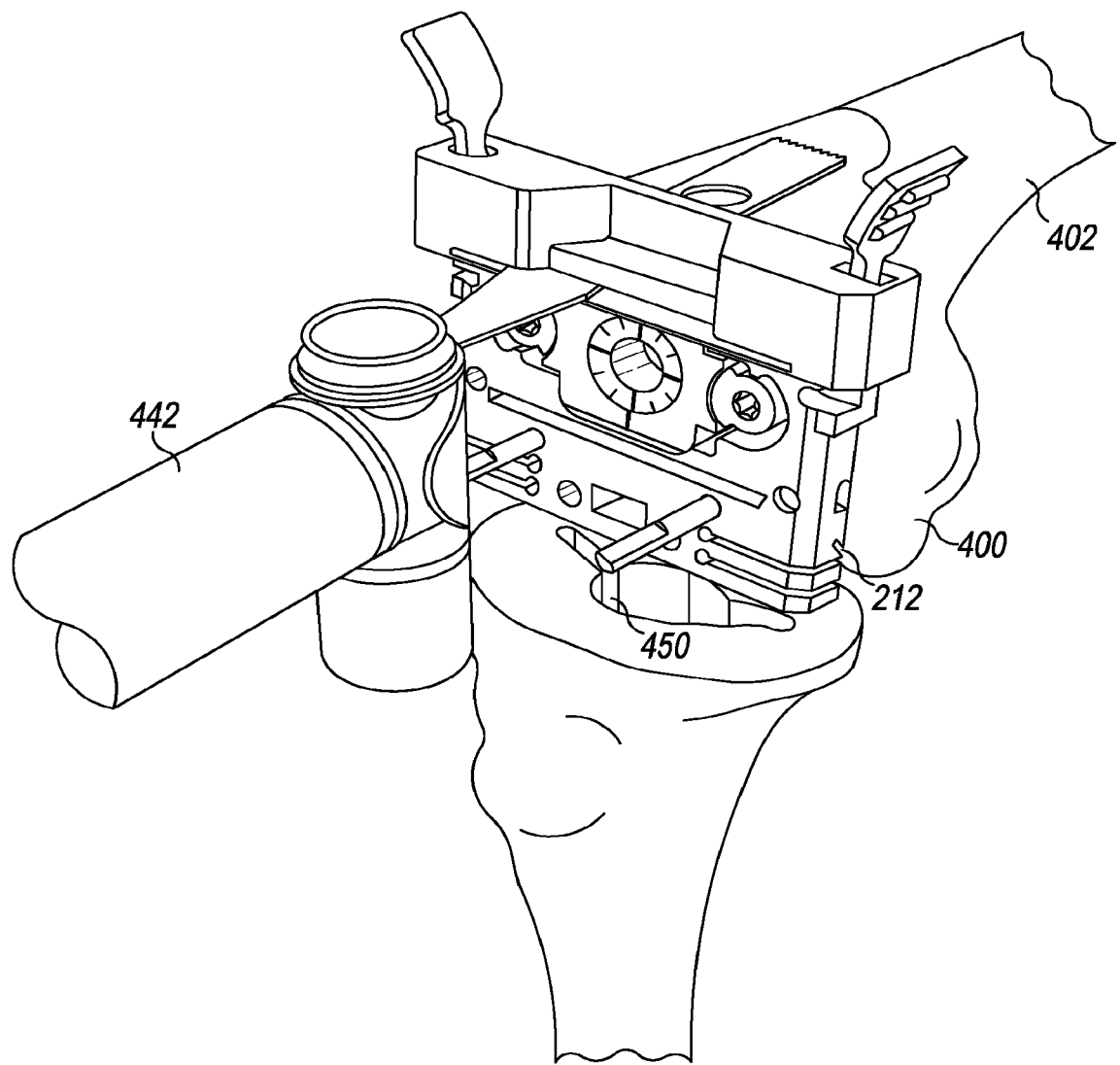

As shown in FIG. 13, the surgeon may then use the anterior cutting block 420 to guide the surgical saw 442 during the performance of an anterior resection. After performing the anterior resection, the surgeon may remove the anterior cutting block 420 from the base cutting block 212. The surgeon may also utilize the cutting guides 232 of the base cutting block 212 to perform a posterior resection of the patient's femur 402.

Figure 14:
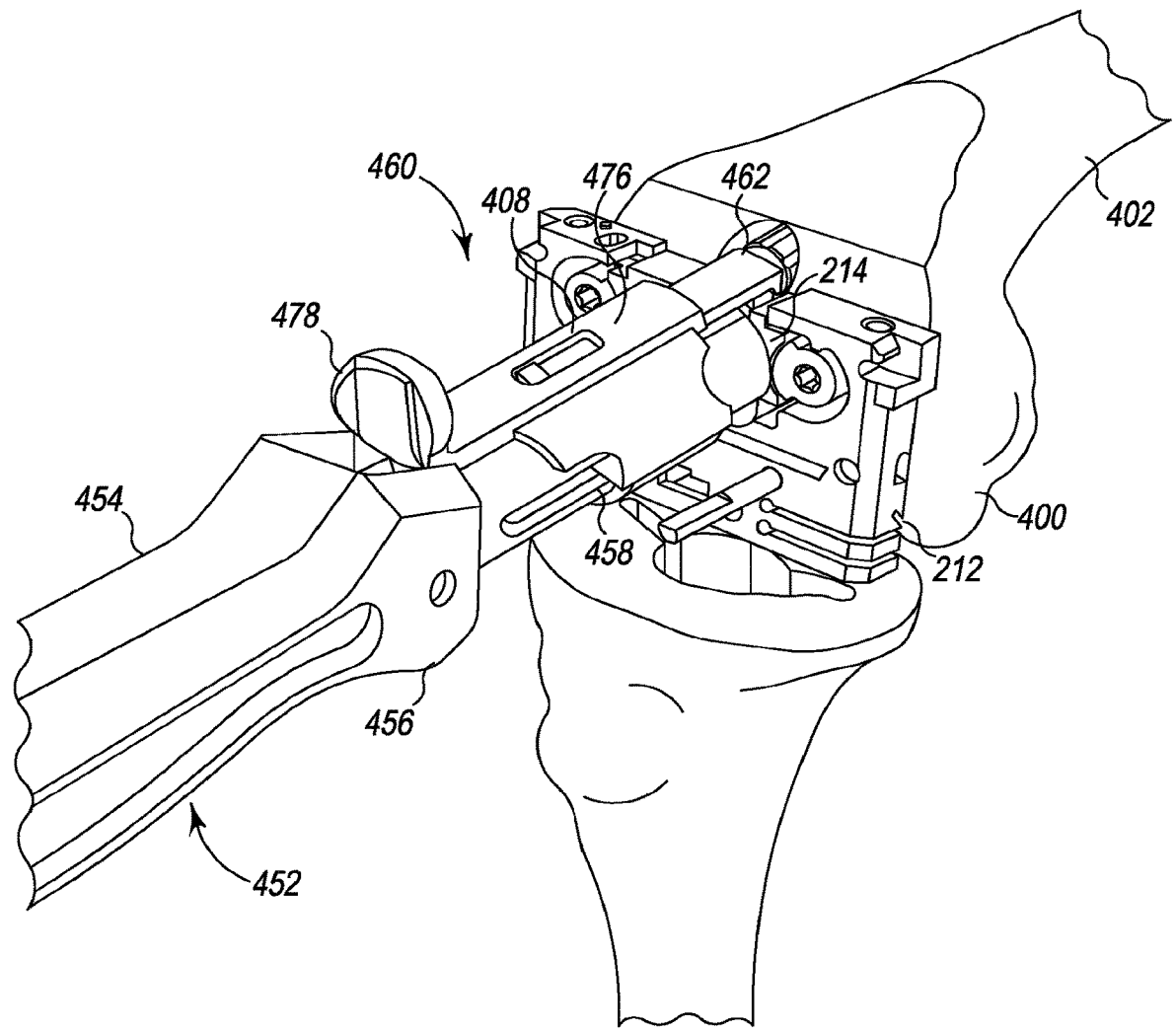
Figure 15:
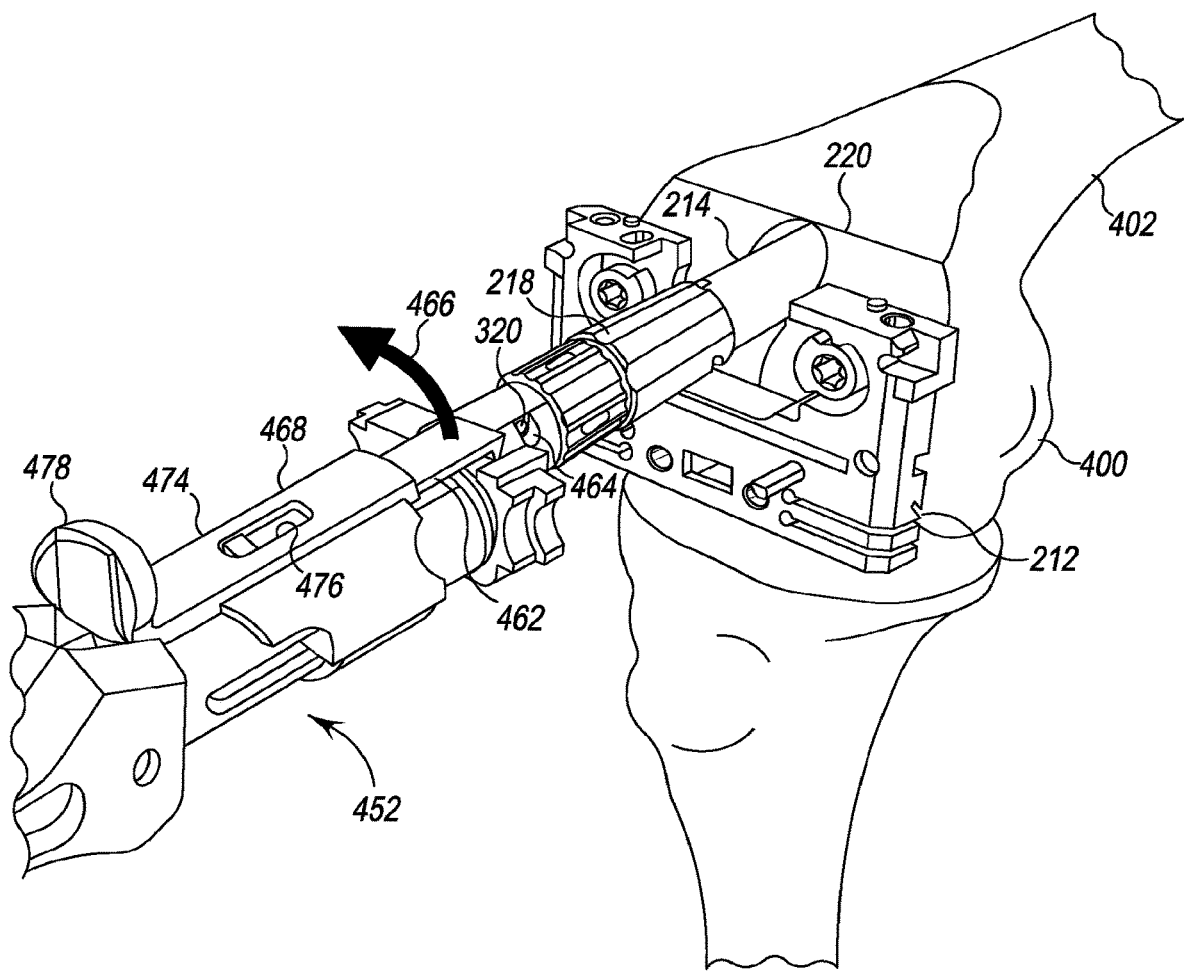

Referring now to FIGS. 14-15, the surgeon may utilize an impaction handle 452 to remove the offset guide assembly 214 from the distal end 400 of the patient's femur 402. The impaction handle 452 includes an elongated body 454. The elongated body 454 is sized and shaped to be gripped by a surgeon during use. The impaction handle 452 also includes a proximal post 458 that extends from the end 456 of the elongated body 454. The proximal post 458 includes a tip (not shown) sized to be positioned in the aperture 280 of the alignment guide assembly 214.

The impaction handle 452 includes an attachment mechanism 460 configured to selectively secure the offset guide assembly 214 to the impaction handle 452. In the illustrative embodiment the attachment mechanism 460 includes a lever arm 462 configured to pivot relative to the proximal post 458. The lever arm 462 includes a locking flange 464 that extends toward tip of the post 458. When the lever arm 462 is pivoted in the direction indicated by arrow 466 in FIG. 15, the locking flange 464 is advanced away from the tip. The lever arm 462 also includes a tab 468 that extends in the direction opposite the locking flange 464.

The attachment mechanism 460 includes a bracket 470 that is configured to slide relative to the post 458 and the elongated body 454. The bracket 470 is illustratively L-shaped and includes a flange 478 that extends away from the proximal post 458. The flange 478 is connected to a slide plate 474 that extends along the post 458. As shown in FIGS. 14 and 15, the slide plate 474 has an oblong slot 476 defined therein, and the tab 468 is positioned in the slot 476.

As shown in FIG. 15, the locking flange 464 engages the head plate 320 of the offset guide assembly 214 to secure the assembly to the handle 452. The surgeon may grip the elongated body 454 to pull the assembly 214 away from the base cutting block 212 and withdraw the stem stabilizer 218 and stem trial 220 from the patient's femur 402.

Figure 16A:
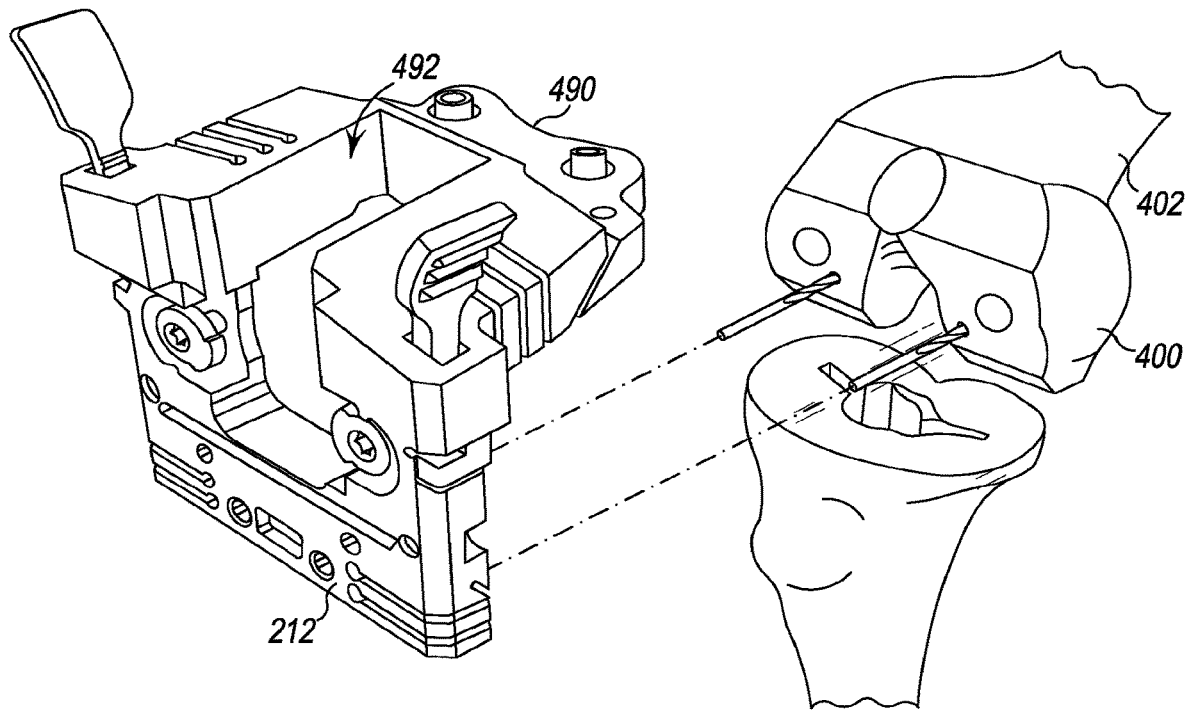
Figure 16B:
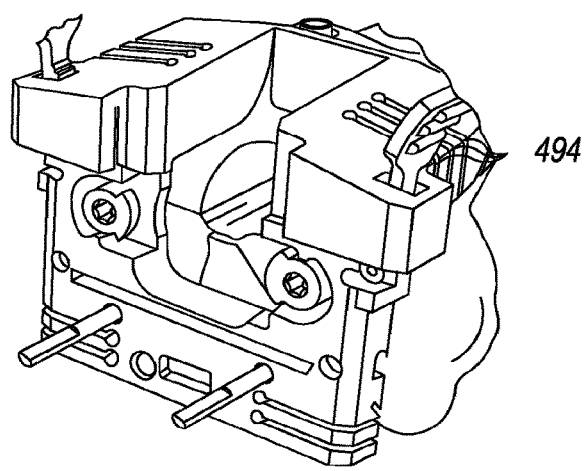

Referring now to FIGS. 16A and 16B, the surgeon may attach a notch cutting block 490 to the mounting platform 236 of the base cutting block 212. The notch cutting block 490 includes a notch cutting guide 492 that is sized to receive a cutting blade of a surgical saw. The notch cutting block 490 also includes a number of distal cutting guides 494 configured to guide the resection of the distal surfaces of the patient's femur 402. With the notch cutting block attached to the base cutting block 212, the surgeon may utilize the saw 442 to make the distal and notch resections of the patient's femur.

Figure 17:
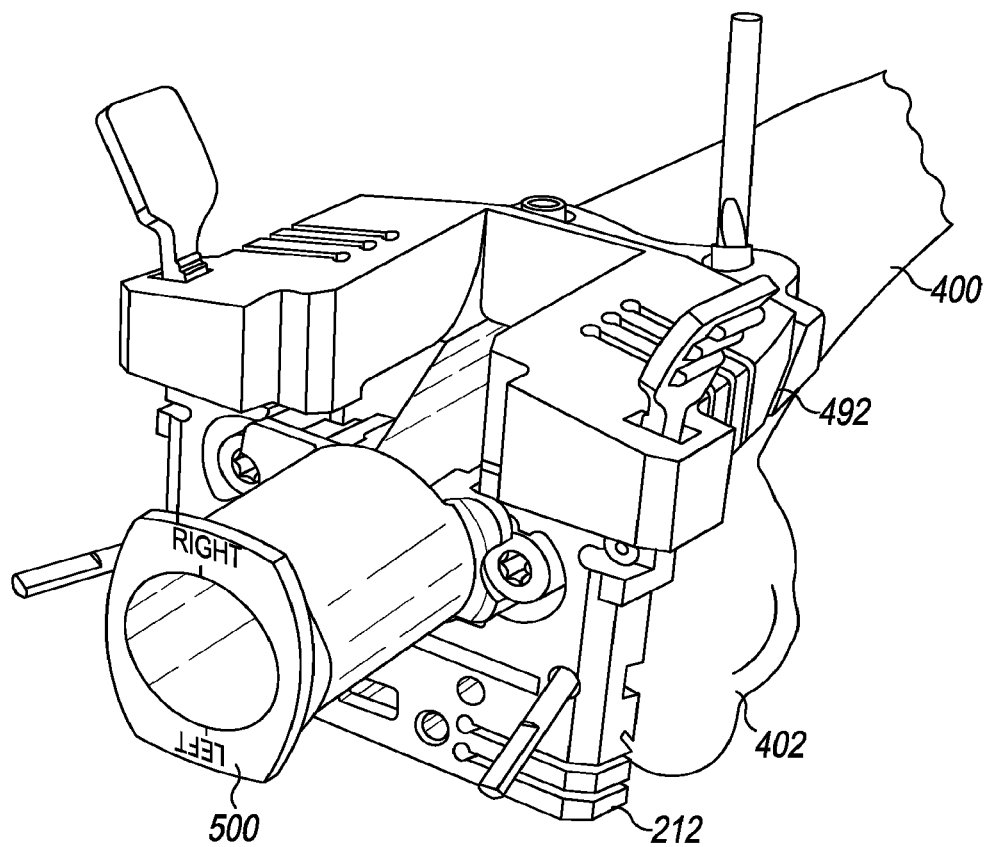

As shown in FIG. 17, surgeon may also utilize a reaming guide 500 with the cutting block 212. To do so, surgeon positions the mounting bracket 300 of the reaming guide 500 in the passageway 228 and operates the locking tabs 240, 242 to secure the reaming guide 500 to the cutting block 212 as shown in FIG. 17. Surgeon may then use one or more reamers to enlarge the opening 406 to receive the offset adapter 92 and the stem component 44 of the femoral prosthetic assembly.

Figure 22:
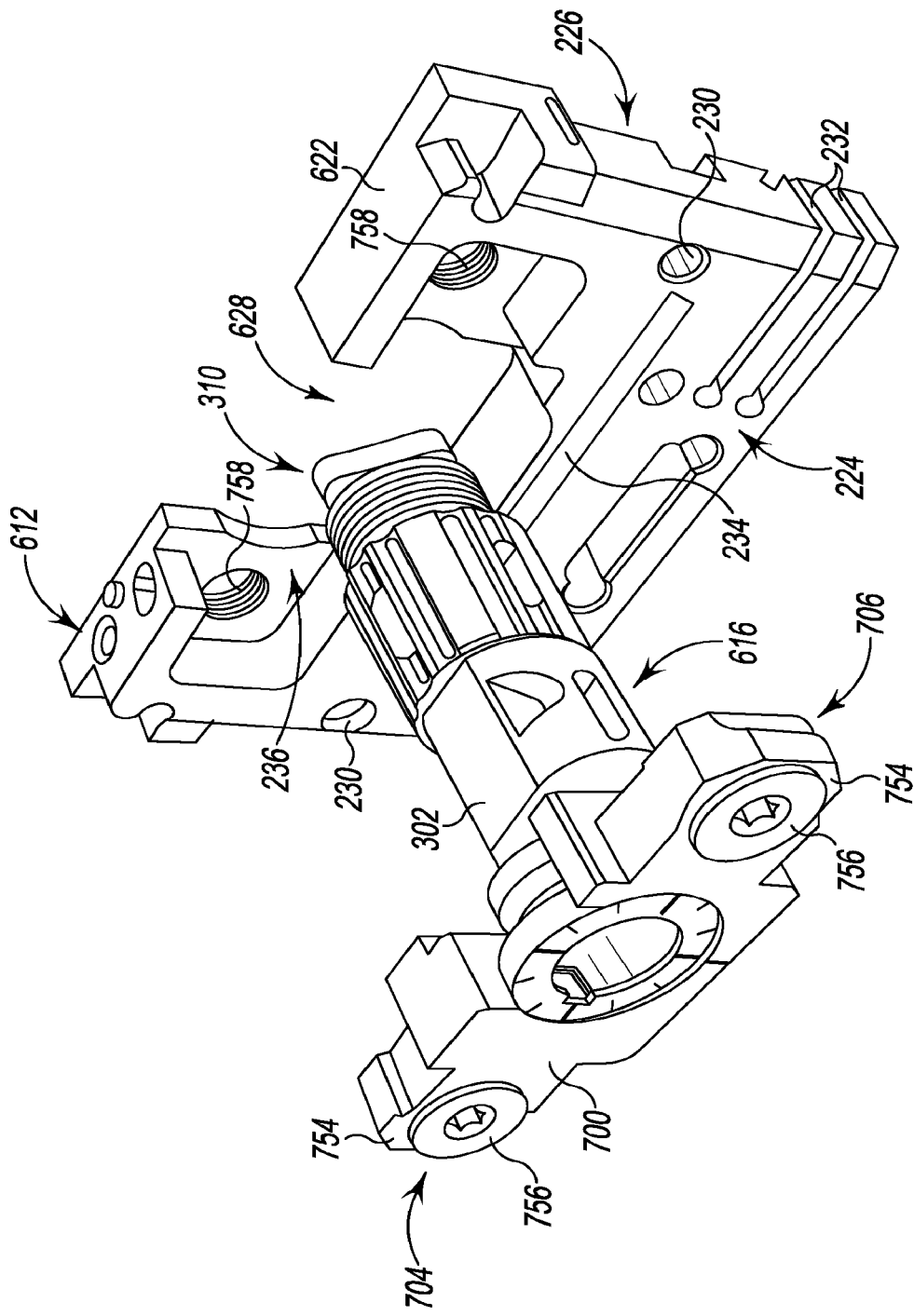
FIG. 22 is an exploded perspective view of another femoral cutting guide assembly of the orthopaedic joint replacement system.
Figure 23:
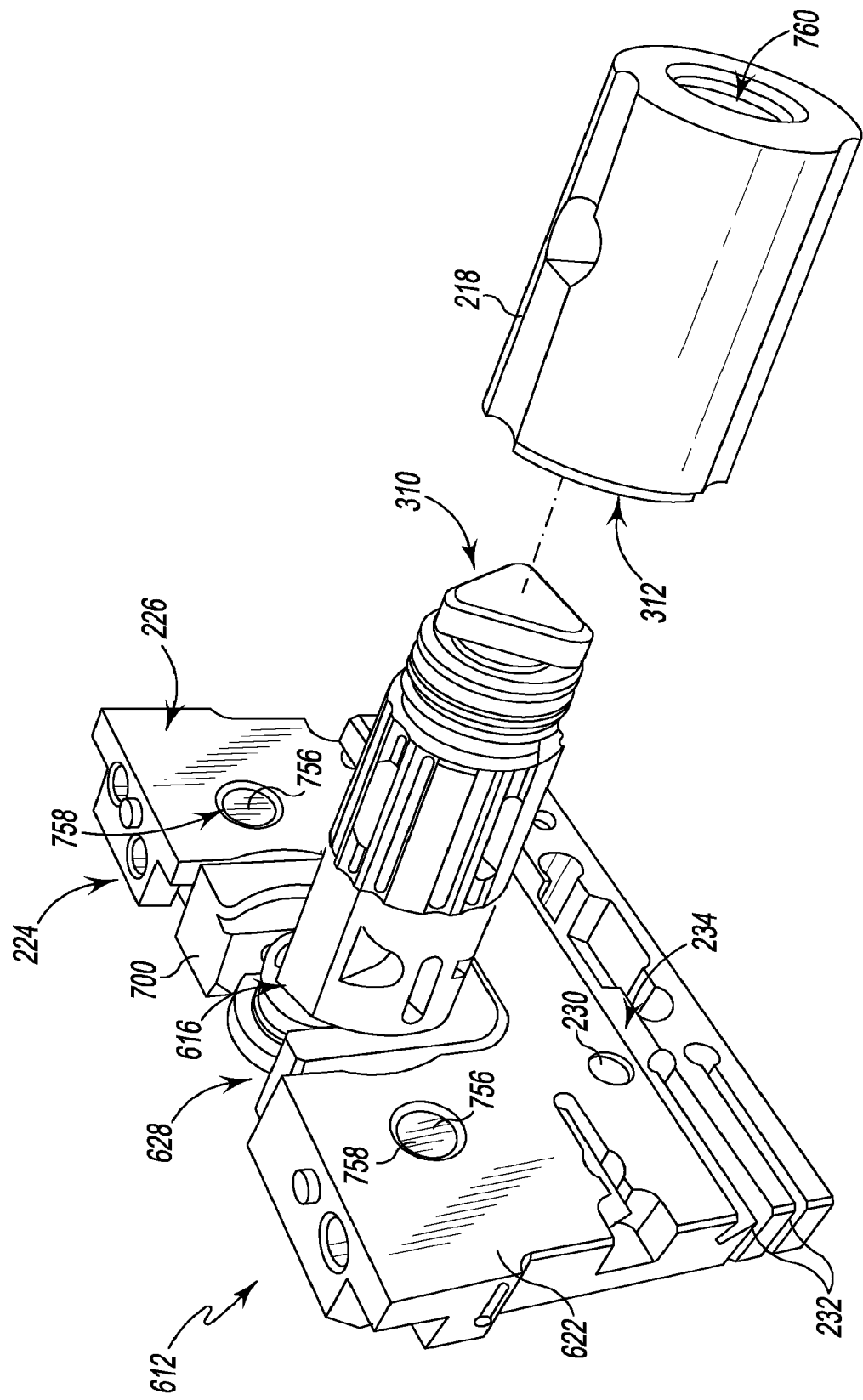
FIG. 23 is an exploded perspective view of the femoral cutting guide assembly of FIG. 22 with the stem stabilizer of FIGS. 18-19.

Referring now to FIGS. 22-23, another embodiment of a base cutting block 612 and an offset guide 616 configured to be secured to the base cutting block 612. The cutting block 612 and the offset guide 616 are similar to the cutting block 212 and the offset guide 616 described above in regard to FIGS. 1-21 and the same reference numbers will be used to identify similar features. The base cutting block 612 includes a base plate 622, which is formed from a metallic material, such as, for example, a stainless steel or cobalt chrome alloy. The base plate includes a distal surface 224 and a proximal surface 226 that is positioned opposite the distal surface. A passageway 628 extends through the surfaces 224, 226. The base cutting block 612 includes a number of fixation pin guide holes 230, which are sized to receive fixation pins 262 to secure the base cutting block to the patient's femur.

The base cutting block 612 includes a number of cutting guides 232, which may be used during the orthopedic surgical procedure to resect a portion of a patient's femur. In the illustrative embodiment, each of the cutting guides 232 is a posterior cutting guide for use in guiding the resection of a posterior surface of the patient's femur. The base cutting block 212 also includes a posterior chamfer cutting guide 234, which may be used to guide the resection of a posterior chamfer surface of the patient's femur. Each guide includes an elongated slot that is sized to receive a cutting saw blade of a surgical saw or other device. The base cutting block 612 also includes a mounting platform 236, which is configured to receive modular cutting guide blocks that may be selectively secured to the base cutting block 212, as described in greater detail below.

The offset guide 616 includes a mounting bracket 700 and an adapter body 302 that is pivotally coupled to the mounting bracket 700. The mounting bracket 700 includes the retaining flanges 754, which are positioned at each of its ends 704, 706. The mounting bracket 700 includes a pair of retained fasteners 756 (illustratively, screws), which are secured to each retaining flange 754, and are received in a pair of threaded bores 758 defined in the cutting block 612 to secure the offset guide 616 to the cutting block 612. It should be appreciated that such fasteners may be retained using washers, various hole diameters, and flange/aperture sizing.

The offset guide 616 has a proximal end 310 that includes a connector having a triangular shape, and, as shown in FIG. 23, the stabilizer 218 is configured to be mounted on the connector end 310, as described above. To assemble the offset guide 216 to the stem stabilizer 218, the surgeon may locate the proximal end 310 in the opening 312 and tighten the threads of the offset guide 216, as described in greater detail below. The stabilizer 218 also has a threaded proximal opening 760 that is sized to receive the threaded distal end 314 of the stem trial 220.

While the foregoing exemplary embodiments have been described to have a separable tibial tray and a tibial tray insert, it is to be understood that the tibial tray may include condyle receiver bearing surfaces that obviate the need for a separate tibial tray insert.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

The invention claimed is:

1. A method of performing an orthopaedic surgical procedure, the method comprising:
    securing an offset guide to an intramedullary orthopaedic surgical instrument by:
        (i) inserting a connector located at a proximal end of the offset guide into an opening defined in a distal end of the intramedullary orthopaedic surgical instrument to prevent relative rotational movement between the proximal end of the offset guide and the intramedullary orthopaedic surgical instrument, and
        (ii) engaging a sleeve with the intramedullary orthopaedic surgical instrument to secure the intramedullary orthopaedic surgical instrument to the offset guide;
    attaching an offset indicator to a distal end of the offset guide by inserting a plug of the offset indicator into a distal aperture defined in the offset guide, wherein inserting the plug of the offset indicator includes receiving an alignment tab of the plug into a corresponding groove of the offset guide; and
    rotating the offset indicator about a longitudinal axis extending parallel to, and spaced apart from, a longitudinal axis defined by the intramedullary orthopaedic surgical instrument to determine an offset orientation for a prosthetic femoral component.

2. The method of claim 1, wherein engaging the sleeve with the intramedullary orthopaedic surgical instrument includes advancing the sleeve toward the proximal end of the offset guide and engaging a threaded outer surface of the sleeve with a threaded inner surface of the intramedullary orthopaedic surgical instrument.

3. The method of claim 2, wherein inserting the connector located at the proximal end of the offset guide into the opening defined in the distal end of the intramedullary orthopaedic surgical instrument includes inserting a triangular-shaped connector into a plurality of slots defined in the threaded inner surface of the intramedullary orthopaedic surgical instrument.

4. The method of claim 1, further comprising securing a stem stabilizer to a stem trial to form the intramedullary orthopaedic surgical instrument.

5. The method of claim 1, further comprising:
    inserting the intramedullary orthopaedic surgical instrument into an opening defined in a distal end of a patient's femur,
    wherein rotating the offset indicator comprises rotating the distal end of the offset guide about the longitudinal axis defined by the intramedullary orthopaedic surgical instrument to determine an offset orientation for the prosthetic femoral component.

6. The method of claim 5, further comprising:
    securing the distal end of the offset guide to a femoral cutting block including a plurality of cutting slots, wherein rotating the offset indicator includes rotating the femoral cutting block relative to a distal surface of the patient's femur.

7. The method of claim 6, further comprising:
attaching a first arm of a femoral positioning block to the femoral cutting block, and positioning a second arm of the femoral positioning block on a proximal end of the patient's tibia such that a predetermined gap is defined between the patient's tibia and the femoral cutting block, wherein rotating the offset indicator includes adjusting a distance between the patient's tibia and the patient's femur while rotating the femoral cutting block relative to the distal surface of the patient's femur.

8. The method of claim 6, further comprising resecting a portion of the distal end of the patient's femur.

9. The method of claim 8, further comprising detaching the offset guide from the femoral cutting block and removing the intramedullary orthopaedic surgical instrument from the opening in the patient's femur.

10. The method of claim 1, further comprising inserting a driver through a passageway defined through the offset indicator and into a socket defined in the distal end of the offset guide.

11. A method of performing an orthopaedic surgical procedure, the method comprising:
securing an offset guide to an intramedullary orthopaedic surgical instrument by:
  (i) aligning a distal end of the intramedullary orthopaedic surgical instrument with a proximal end of the offset guide,
  (ii) positioning a connector located at the proximal end of the offset guide into an opening defined in the distal end of the intramedullary orthopaedic surgical instrument to prevent relative rotational movement between the proximal end of the offset guide and the intramedullary orthopaedic surgical instrument, and
  (iii) engaging a sleeve with the intramedullary orthopaedic surgical instrument to secure the intramedullary orthopaedic surgical instrument to the offset guide;
inserting the offset guide and the intramedullary orthopaedic surgical instrument through a passageway defined through a femoral cutting block including a plurality of cutting slots;
positioning a pair of retaining flanges of the offset guide into a corresponding pair of apertures located on opposing sides of the passageway defined through the femoral cutting block; and
rotating a pair of locking tabs of the femoral cutting block to a locked position in which each locking tab engages a corresponding retaining flange of the offset guide to secure the offset guide to the femoral cutting guide.

12. The method of claim 11, wherein rotating the pair of locking tabs of the femoral cutting block comprises rotating each locking tab from an unlocked position in which an ear of the corresponding locking tab faces away from the passageway defined through the femoral cutting block to the locked position in which the ear of the corresponding locking tab faces toward the passageway defined through the femoral cutting block.

13. The method of claim 12, wherein rotating each locking tab to the locked position comprises rotating each locking tab to the locked position such that the ear of the corresponding lock tab is positioned over the corresponding retaining flange of the offset guide.

14. The method of claim 11, wherein engaging the sleeve with the intramedullary orthopaedic surgical instrument includes advancing the sleeve toward the proximal end of the offset guide and engaging a threaded outer surface of the sleeve with a threaded inner surface of the intramedullary orthopaedic surgical instrument.

15. The method of claim 11, wherein positioning the connector at the proximal end of the offset guide in the opening defined in the distal end of the intramedullary orthopaedic surgical instrument includes positioning a triangular-shaped connector into a plurality of slots defined in the threaded inner surface of the intramedullary orthopaedic surgical instrument.

16. The method of claim 11, further comprising securing a stem stabilizer to a stem trial to form the intramedullary orthopaedic surgical instrument.

17. The method of claim 11, further comprising:
inserting the intramedullary orthopaedic surgical instrument into an opening defined in a distal end of a patient's femur, and
rotating a distal end of the offset guide about a longitudinal axis extending through the intramedullary orthopaedic surgical instrument to determine an offset orientation for a prosthetic femoral component.

18. The method of claim 17, further comprising:
attaching an offset indicator to the distal end of the offset guide,
wherein rotating the distal end of the offset guide includes rotating the offset indicator about a second longitudinal axis extending parallel to, and spaced apart from, the longitudinal axis extending through the intramedullary orthopaedic surgical instrument.

19. The method of claim 18, further comprising:
attaching a first arm of a femoral positioning block to the femoral cutting block, and positioning a second arm of the femoral positioning block on a proximal end of the patient's tibia such that a predetermined gap is defined between the patient's tibia and the femoral cutting block,
wherein rotating the distal end of the offset guide includes adjusting a distance between the patient's tibia and the patient's femur while rotating the femoral cutting block relative to a distal surface of the patient's femur.

\* \* \* \* \*